US006955675B2

(12) United States Patent
Jain

(10) Patent No.: US 6,955,675 B2
(45) Date of Patent: Oct. 18, 2005

(54) ABLATION CATHETER WITH TRANSDUCER FOR PROVIDING ONE OR MORE OF PRESSURE, TEMPERATURE AND FLUID FLOW DATA FOR USE IN CONTROLLING ABLATION THERAPY

(75) Inventor: Mudit K. Jain, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 10/037,663

(22) Filed: Jan. 3, 2002

(65) Prior Publication Data

US 2002/0123749 A1 Sep. 5, 2002

Related U.S. Application Data

(63) Continuation-in-part of application No. 09/797,435, filed on Mar. 1, 2001, now Pat. No. 6,666,862.

(51) Int. Cl.[7] ............................................. A61B 18/18
(52) U.S. Cl. ........................... 606/41; 607/101; 607/102
(58) Field of Search ........................ 606/41–43, 45–50, 606/34; 607/99, 101, 113, 116, 119, 122

(56) References Cited

U.S. PATENT DOCUMENTS

| 6,049,737 | A |   | 4/2000 | Simpson et al. |
| 6,063,022 | A | * | 5/2000 | Ben-Haim ................. 600/41 |
| 6,200,310 | B1 | * | 3/2001 | Ben-Haim et al. ........... 606/10 |
| 6,241,724 | B1 | * | 6/2001 | Fleischman et al. ......... 606/41 |
| 6,287,297 | B1 | * | 9/2001 | Woodruff et al. ............. 606/7 |
| 6,391,024 | B1 | * | 5/2002 | Sun et al. .................... 606/34 |
| 6,569,160 | B1 | * | 5/2003 | Goldin et al. ................ 606/41 |
| 6,592,580 | B1 | * | 7/2003 | Stockert ...................... 606/41 |
| 2001/0002000 | A1 |   | 5/2001 | Kumar et al. |
| 2002/0002372 | A1 |   | 1/2002 | Jahns et al. |

FOREIGN PATENT DOCUMENTS

| WO | WO 96/36282 | 11/1996 |
| WO | WO 97/17014 | 5/1997 |
| WO | WO 00/51511 | 9/2000 |
| WO | WO 00/51513 | 9/2000 |

OTHER PUBLICATIONS

Mudit K. Jain, "An Experimental and Numerical Analysis of the Spatiotemporal Behavior of Radiofrequency Ablation," Deparment of biomedical Engineering, Duke University, UMI Microform #9942512, (1999) UMI Company, Ann Arbor, MI.

Helen Høgh Petersen, MD et al, "Lesion Dimensions During Temperature–Controlled Radiofrequency Catheter Ablaton of Left Ventricular Porcine Myocardium", Circulation Journal of the american heart Association, vol. 99, No. 2, Jan. 19, 1999, pp 319–325,; USA.

(Continued)

Primary Examiner—Roy D. Gibson
(74) Attorney, Agent, or Firm—Fulwider Patton Lee & Utecht, LLP

(57) ABSTRACT

A distal segment of a catheter shaft is adapted to be positioned against tissue in a biological organ. The distal segment has a tissue-contacting area intended to contact the tissue. One or more pressure sensors positioned within the tissue-contacting area provide pressure data indicative of the pressure exerted on the distal segment. The distal segment carries one or more electrodes and the pressure sensors are located either on an electrode or on the catheter shaft near an electrode. The pressure sensors provide pressure data to a processor that analyzes the data to determine if the tissue-contacting area of the distal segment is contacting the tissue. The pressure sensors may also provide temperature data indicative of the temperature at the sensor. A flow sensor, located opposite the pressure sensor on the shaft, provides data related to the flow rate of fluid through the organ.

46 Claims, 15 Drawing Sheets

OTHER PUBLICATIONS

David E. Haines, "The Biophysics of Radiofrequency Catheter Ablation in the Heart: The Importance of Temperature Monitoring;," Pacing And Clinical Electrophysicology, Mar. 1993, vol. 16, No. 3, Part II, pp 586–591; Futura Publishing Company, Inc., Mt. Kisco, NY.

David E. Haines et al., "Tissue Heating During Radiofrequency Catheter Ablation: A Thermodynamic Model and Observations in Isolated Perfused and Superfused Canine Right Ventricular Free Wall," Pacing And Clinical Eletrophysicology, Jun. 1989, vol. 12, No. 6, pp 962–976; Futura Publishing Company, Inc., Mt. Kisco, NY.

* cited by examiner

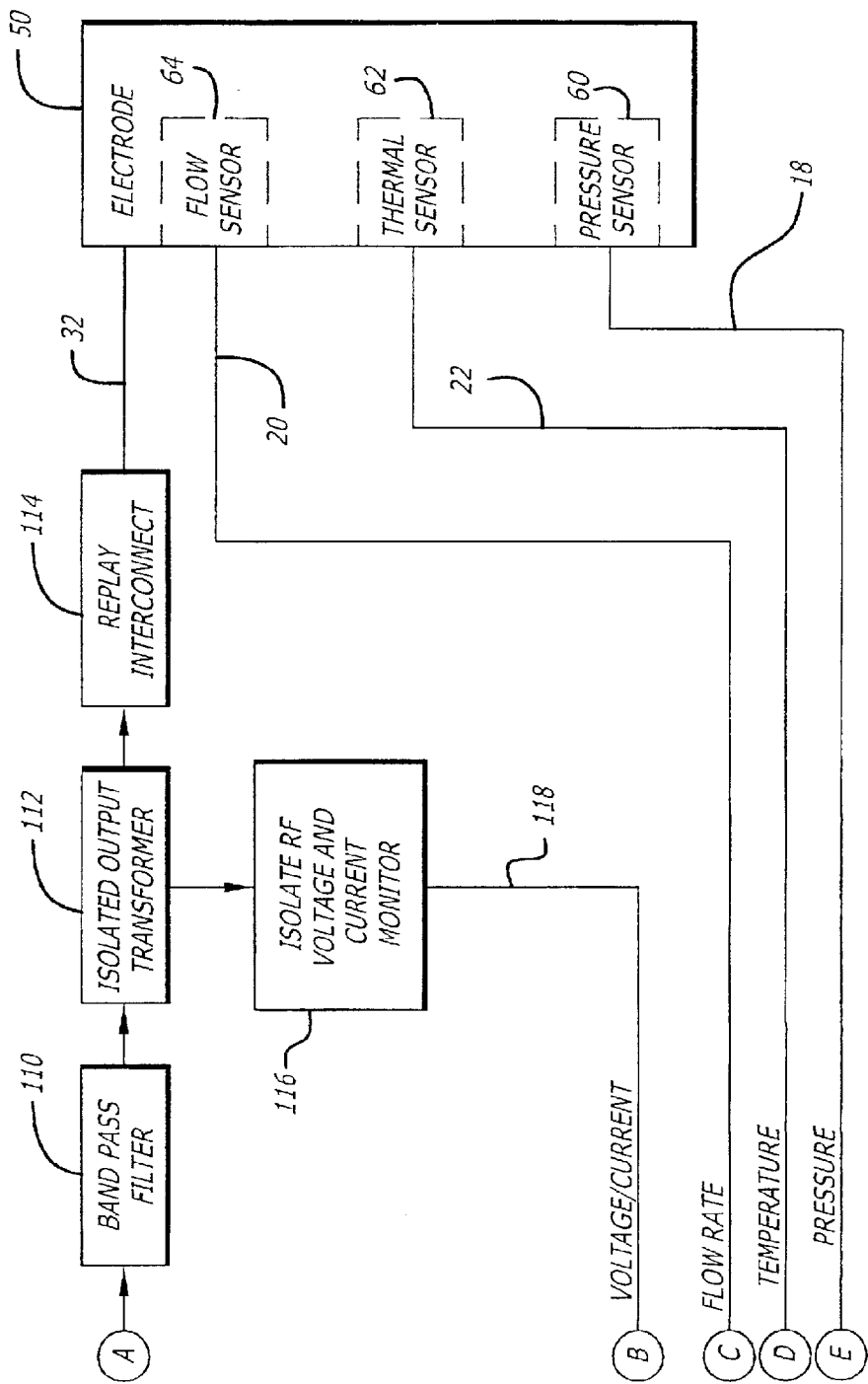

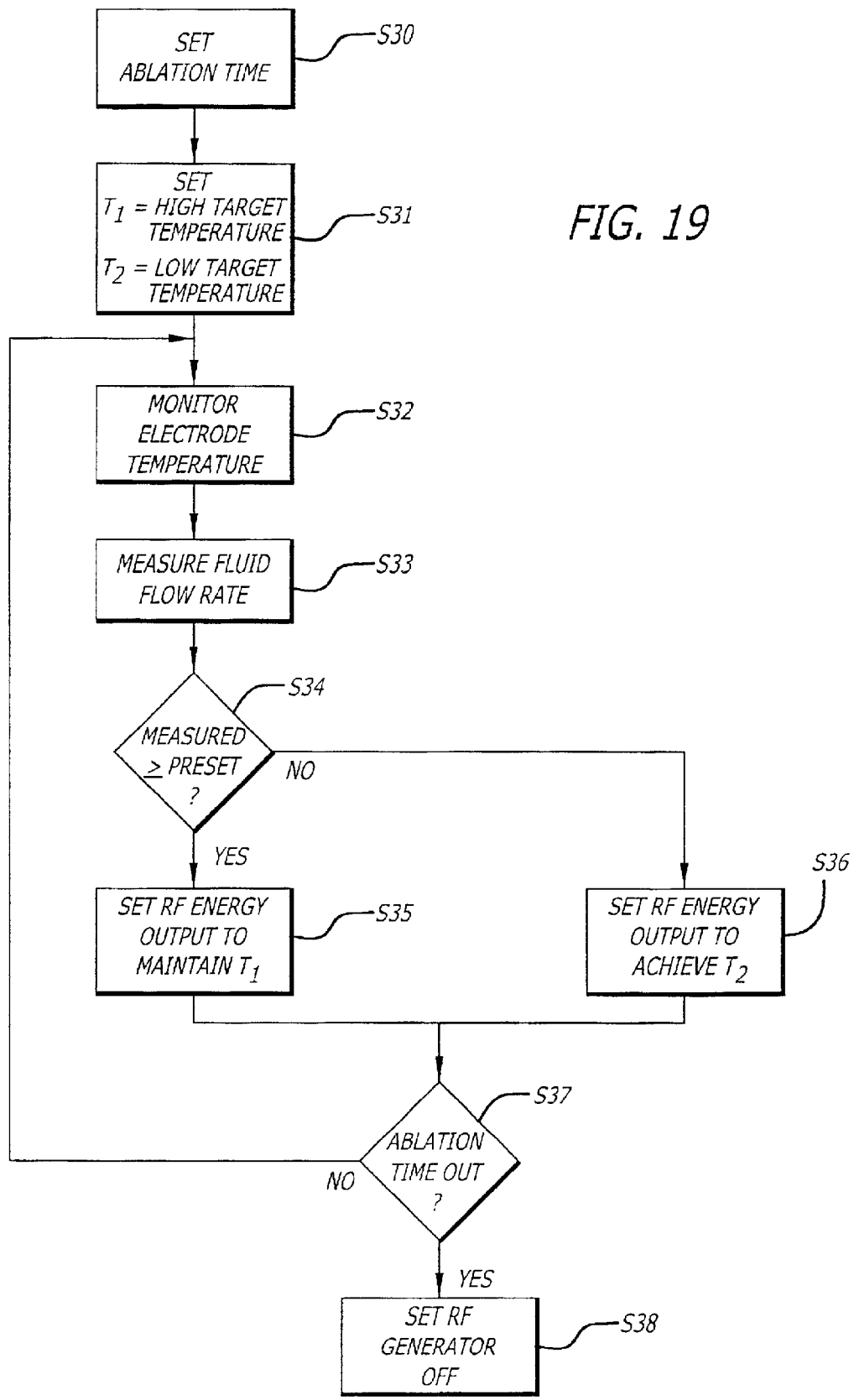

ABLATION CATHETER WITH TRANSDUCER FOR PROVIDING ONE OR MORE OF PRESSURE, TEMPERATURE AND FLUID FLOW DATA FOR USE IN CONTROLLING ABLATION THERAPY

RELATED APPLICATIONS

This is a continuation-in-part of application Ser. No. 09/797,435, filed Mar. 1, 2001 now U.S. Pat. No. 6,666,862.

BACKGROUND OF THE INVENTION

1. Field of the Invention

The invention relates generally to an electrophysiological ("EP") catheter system and method for providing energy to biological tissue within a biological site, and more particularly, to an EP system and method for assessing the adequacy of contact between the catheter and tissue and controlling the delivery of RF energy to the tissue based on the flow of fluid through the biological site.

2. Description of the Related Art

The heart beat in a healthy human is controlled by the sinoatrial node ("SA node") located in the wall of the right atrium. The SA node generates electrical signal potentials that are transmitted through pathways of conductive heart tissue in the atrium to the atrioventricular node ("AV node") which in turn transmits the electrical signals throughout the ventricle by means of the His and Purkinje conductive tissues. Improper growth, remodeling, or damage to, the conductive tissue in the heart can interfere with the passage of regular electrical signals from the SA and AV nodes. Electrical signal irregularities resulting from such interference can disturb the normal rhythm of the heart and cause an abnormal rhythmic condition referred to as "cardiac arrhythmia."

While there are different treatments for cardiac arrhythmia, including the application of anti-arrhythmia drugs, in many cases ablation of the damaged tissue can restore the correct operation of the heart. Such ablation can be performed percutaneously, a procedure in which a catheter is introduced into the patient through an artery or vein and directed to the atrium or ventricle of the heart to perform single or multiple diagnostic, therapeutic, and/or surgical procedures. In such case, an ablation procedure is used to destroy the tissue causing the arrhythmia in an attempt to remove the electrical signal irregularities or create a conductive tissue block to restore normal heart beat. Successful ablation of the conductive tissue at the arrhythmia initiation site usually terminates the arrhythmia or at least moderates the heart rhythm to acceptable levels. A widely accepted treatment for arrhythmia involves the application of RF energy to the conductive tissue.

In the case of atrial fibrillation ("AF"), a procedure published by Cox et al. and known as the "Maze procedure" involves the formation of continuous atrial incisions to prevent atrial reentry and to allow sinus impulses to activate the entire myocardium. While this procedure has been found to be successful, it involves an intensely invasive approach. It is more desirable to accomplish the same result as the Maze procedure by use of a less invasive approach, such as through the use of an appropriate EP catheter system providing RF ablation therapy. In this therapy, transmural ablation lesions are formed in the atria to prevent atrial reentry and to allow sinus impulses to activate the entire myocardium. In this sense transmural is meant to include lesions that pass through the atrial wall or ventricle wall from the interior surface (endocardium) to the exterior surface (epicardium).

There are two general methods of applying RF energy to cardiac tissue, unipolar and bipolar. In the unipolar method a large surface area electrode; e.g., a backplate, is placed on the chest, back or other external location of the patient to serve as a return. The backplate completes an electrical circuit with one or more electrodes that are introduced into the heart, usually via a catheter, and placed in intimate contact with the aberrant conductive tissue. In the bipolar method, electrodes introduced into the heart have different potentials and complete an electrical circuit between themselves. In both the unipolar and the bipolar methods, the current traveling between the electrodes of the catheter and between the electrodes and the backplate enters the tissue and induces a temperature rise in the tissue resulting in ablation.

During ablation, RF energy is applied to the electrodes to raise the temperature of the target tissue to a lethal, non-viable state. In general, the lethal temperature boundary between viable and non-viable tissue is between approximately 45° C. to 55° C. and more specifically, approximately 48° C. Tissue heated to a temperature above 48° C. for several seconds becomes permanently non-viable and defines the ablation volume. Tissue adjacent to the electrodes delivering RF energy is heated by resistive heating which is conducted radially outward from the electrode-tissue interface. The goal is to elevate the tissue temperature, which is generally at 37° C., fairly uniformly to an ablation temperature above 48° C., while keeping both the temperature at the tissue surface and the temperature of the electrode below 100° C. In clinical applications, the target temperature is set below 70° C. to avoid coagulum formation. Lesion size has been demonstrated to be proportional to temperature.

In order to produce effective transmural lesions it is necessary to ensure that the electrodes are in intimate contact with the tissue. Positioning of the electrodes is typically done visually under fluoroscopy imaging and is thus largely a function of a physician's training and experience. Assessment of adequate electrode/tissue contact is somewhat of an art and verification, at present, is typically inferred through comparison of pre- and post-ablation electrocardiogram ("ECG") analysis.

The use of impedance as an indication of electrode/tissue contact has been reported in the treatment of focal arrhythmias, such as ventricular tachyarrhythmia. In these procedures, a catheter with a single combination ablation/impedance-measuring tip electrode is inserted into the local blood pool within the heart and an impedance measurement is taken. The tip electrode is then placed at an ablation location and, so as to push the tip electrode deep into the cardiac tissue, force is applied along the axis of the catheter. An impedance measurement is then taken and compared to the impedance of the blood pool. This subsequent impedance measurement is referred to as a "contact-assessment" impedance. A significant increase in the contact-assessment impedance relative the blood-pool impedance serves as an indication that the tip electrode is in contact with cardiac tissue.

In this procedure a significant increase in impedance is noted due to the fact that the tip electrode is pushed deep into the cardiac tissue and is thus largely surrounded by tissue, as opposed to blood. While this electrode/tissue contact assessment technique is effective for the treatment of focal arrhythmias, it is less effective for the treatment of non-focal arrhythmias, such as atrial fibrillation. Ablation therapy for atrial fibrillation often involves the formation of transmural linear lesions. In this form of ablation therapy a linear array of band electrodes is placed against the atrial wall. While the band electrodes are held against the tissue with some degree of force, a portion of the band electrodes is likely to remain in the blood pool. The presence of blood against a portion of the band electrode affects the impedance measurement and reduces the significance of the difference between the blood-pool impedance and the contact-assessment impedance. Thus, the above-described electrode/tissue contact assessment technique that relies on the use of a tip electrode forced into the tissue is ineffective for linear ablation therapy. This known technique is further ineffective for linear ablation because it does not account for fluctuations in impedance measurements which may occur due to movement of electrodes caused by respiration and heart contractions.

Blood coagulation is a major limitation/complication associated with RF ablation therapy. Coagulation can lead to thromboembolism and also form an insulating layer around the electrode hindering further energy delivery required for ablation therapy. Thus, heating of blood is a major concern for ablation safety and efficacy. During ablation therapy, it is known that the temperature of blood near an electrode is dependent on the blood flow rate. Low blood flow results in reduced convective heat dissipation within the blood pool around the electrode and thus higher blood temperature. Conversely, high blood flow rate results in increased convective heat dissipation within the blood pool around the electrode and thus a lower blood temperature.

Conventional RF ablation systems fail to account for the effect that varying blood flow rates have on blood, electrode and tissue temperatures, which can be substantial. During an ablation procedure, conventional systems apply a level of RF energy to the electrodes sufficient to elevate the tissue temperature to a level that causes the tissue to become nonviable. The level of RF energy is generally constant regardless of the blood flow rate and is only adjusted if the system employs some type of temperature feedback control. In these systems an attempt is made to guard against blood coagulation and coagulum formation by monitoring the temperature of the electrodes, usually using a thermocouple attached to the electrode. When a threshold temperature is reached, the application of RF energy is either reduced or shut off. However, such thermocouples are generally located at the tissue/electrode contact location, which can have a significantly different temperature than the opposite side of the electrode that is in the blood pool.

Such systems tend either to have a high incidence of coagulation or to operate inefficiently. Coagulation is likely to occur in these systems when the RF energy delivered to the electrode is set to an ablation-inducing level during periods of high-blood flow. The temperature sensing thermocouple does not provide the system with sufficient information about the temperature of the blood pool. Consequently, the convective heat dissipation effect of the high-blood flow keeps the blood pool around the electrode cool and ablation is efficiently accomplished, however, during periods of low-blood flow, the reduced convective heat dissipation allows the blood pool to heat. Over the course of an ablation procedure, the cumulative effect of the periods of low-blood flow is likely to result in coagulum formation.

In order to avoid coagulation the energy level may be reduced. This, however, tends to lead to an inefficient ablation procedure. If the energy level is set to induce ablation during periods of low flow, the convective heat dissipation effect during periods of high-blood flow reduces the electrode temperature and thus the tissue temperature to a non-ablative level. The culmination of these periods of non-ablative temperature levels at best increases the amount of time necessary to achieve an ablation-inducing temperature and thus the overall procedure time, and at worst prevents the electrode from ever reaching an ablation-inducing level.

Hence, those skilled in the art have recognized a need for a RF ablation system and method that assesses the adequacy of electrode-tissue contact independent of impedance measurements and controls and adjusts the RF energy level delivered to tissue within a biological site based on the flow rate of fluid through the site. The invention fulfills this need and others.

SUMMARY OF THE INVENTION

Briefly, and in general terms, the invention is directed to an EP catheter system and method for assessing the adequacy of contact between the catheter and tissue and controlling the delivery of RF energy to the tissue based on the flow of fluid through the biological site.

In one aspect, the invention relates to a catheter for use during treatment of biological tissue within a biological organ having fluid flowing therethrough. The catheter includes a shaft having a distal segment that is adapted to be positioned in the biological organ. The distal segment has a tissue-contacting area that is intended to contact the biological tissue. The catheter also includes at least one pressure sensor associated with the distal segment. The pressure sensor is positioned within the tissue-contacting area and is adapted to provide pressure data indicative of the pressure exerted on the distal segment at or near the pressure sensor.

In another aspect, the invention is related to a system for applying energy to biological tissue within a biological organ having fluid flowing therethrough. The system includes a generator for providing energy and a catheter carrying an electrode system at its distal segment. The distal segment has a tissue-contacting area that is adapted to be positioned in the biological organ and intended to contact the biological tissue. The electrode system is adapted to receive energy from the generator. The system also includes at least one pressure sensor that is associated with the distal segment and is located within the tissue-contacting area. The pressure sensor is adapted to provide pressure data indicative of the pressure exerted on the distal segment at or near the pressure sensor. A processor is responsive to the pressure data and is configured to analyze the pressure data to provide an indication of contact between the distal segment at or near the pressure sensor and the tissue.

In another facet, the invention is related to a system for assessing the adequacy of contact between an electrode and biological tissue within a biological organ having biological fluid therein. The system includes a pressure sensor configured to provide a reference pressure indicative of the pressure at the electrode when the electrode is positioned in the biological fluid. The pressure sensor is also configured to provide an assessment pressure indicative of the pressure at the electrode when the electrode is positioned proximal the biological tissue. The system also includes a processor that is responsive to the reference and assessment pressure signals. The processor is configured to analyze the pressure signals and indicate the state of electrode/tissue contact.

In another facet, the invention is related to a method of assessing the adequacy of contact between an electrode and biological tissue within a biological organ having biological fluid therein. The electrode is positioned in the biological fluid to obtain a reference pressure value indicative of the pressure exerted on a region on or near the electrode. The electrode is moved to a position proximal the biological tissue. An assessment pressure value is obtained by measuring the pressure exerted on the region on or near the electrode. The assessment pressure and the reference pressure are analyzed and the state of electrode/tissue contact is indicated.

In yet another aspect, the invention is related to a system for assessing the adequacy of contact between an electrode and biological tissue within a biological organ having biological fluid therein. The system includes a pressure sensor that is configured to provide assessment pressure values indicative of the pressure at the electrode. The system also includes a processor that is adapted to sample a sequence of pressure values for a given time period and monitor the sequence of pressure values for variations indicative of electrode/tissue contact.

In other facets, the invention involves methods of assessing the adequacy of contact between an electrode and biological tissue within a moving biological organ having biological fluid therein. The electrode is positioned proximal to the biological tissue. A sequence of pressure values are obtained by periodically measuring the pressure at the electrode during the time period. The sequence of pressure values are monitored for variations indicative of electrode/tissue contact. In another method, a reference pressure value for each of a plurality of electrodes is obtained by positioning the plurality of electrodes in the biological fluid and measuring the pressure exerted at each electrode by the biological fluid. The plurality of electrodes are moved to a position proximal the biological tissue. For each of the electrodes an assessment pressure value is obtained by measuring the pressure exerted at each electrode. The assessment impedance and the reference impedance for each electrode are analyzed and the state of electrode/tissue contact is indicated.

These and other aspects and advantages of the invention will become apparent from the following detailed description and the accompanying drawings which illustrate by way of example the features of the invention.

BRIEF DESCRIPTION OF THE DRAWINGS

FIGS. 11A and 11B form a block diagram presenting a detailed configuration of one embodiment of the ablation system of FIG. 1;

FIG. 19 is a flow chart of an alternate operation of the ablation system when in the automatic temperature controlled mode.

DETAILED DESCRIPTION OF THE PREFERRED EMBODIMENTS

Figure 1:
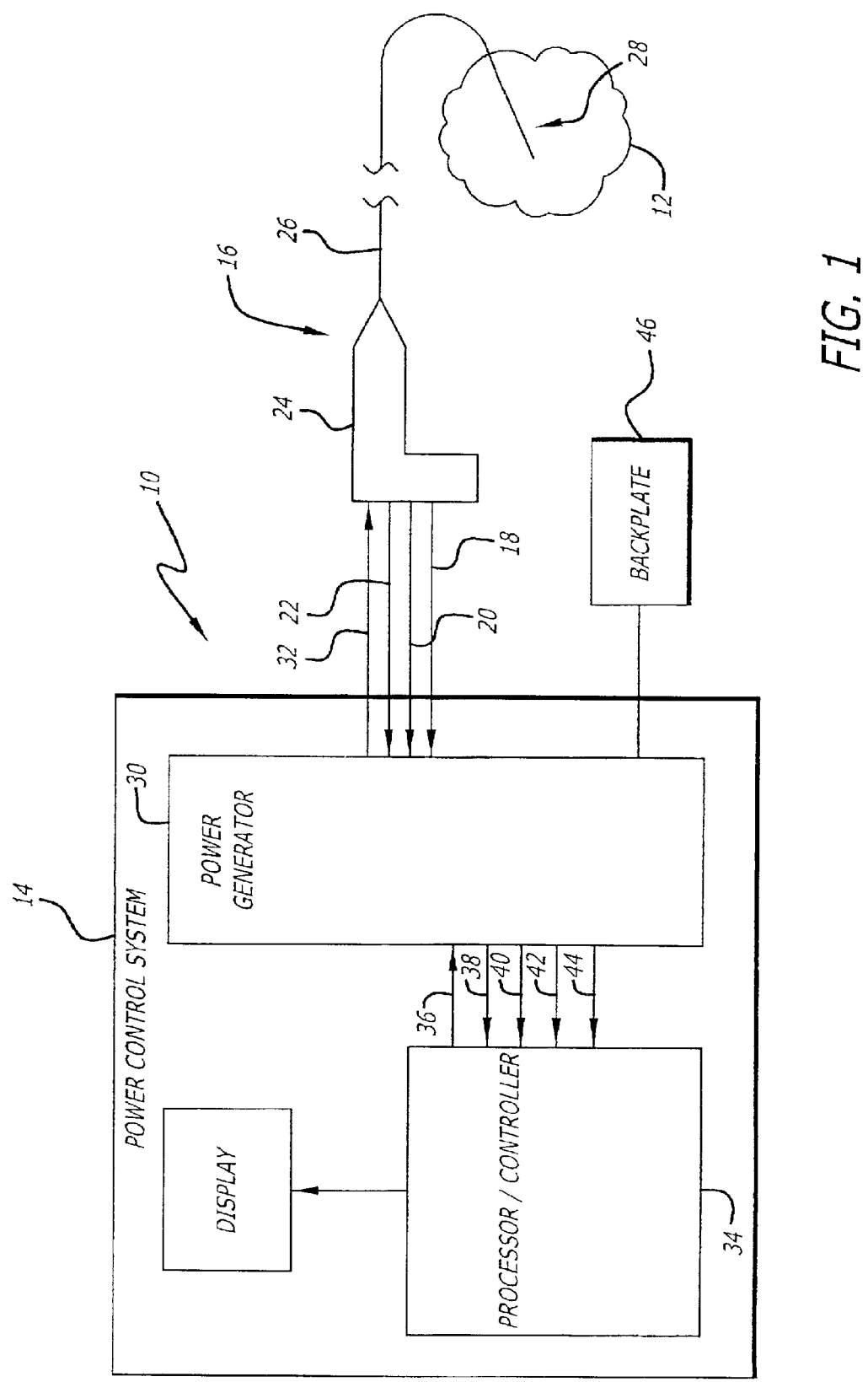
FIG. 1 is a schematic block diagram of an ablation system configured in accordance with aspects of the invention including a power control system a catheter system and a backplate.

Turning now to the drawings, in which like reference numerals are used to designate like or corresponding elements among the several figures, in FIG. 1 there is shown a system 10 for use in ablation therapy of a biological site 12, e. g., the atrium or ventricle of the heart. The system 10 includes a power control system 14, a catheter system 16 having means (not shown) for providing one or more of pressure data 18, flow-rate data 20 and temperature data 22 to the power control system 14. The catheter system 16 includes a handle 24 and a steerable catheter shaft 26 having a distal segment 28. The distal segment 28 carries an electrode system (not shown) and is capable of being percutaneously introduced into a biological site 12. The pressure data 18 includes data indicative of the pressure being exerted on the distal segment 28 in the region of the electrode system while the flow-rate data 20 includes data indicative of the rate of fluid flow through the biological site 12, such as blood through the heart, in the region of the electrode system. The temperature data 22 includes data indicative of the temperature at the electrode system.

The power control system 14 includes a power generator 30, that may have any number of output channels through which it provides power 32 to the catheter system 16. The operation of the power generator 30 is controlled by a processor/controller 34 which outputs control signals 36 to the power generator 30. The processor/controller 34 monitors the power 32 provided by the power generator 30 along a power monitor line 38. In addition, the processor/controller 34 also receives one or more of the pressure data 18, flow-rate data 20 and temperature data 22, from the catheter system 16 over a pressure monitor line 40, flow rate monitor line 42 and temperature monitor line 44, respectively. Using the pressure data 18 the processor/controller 34 determines if there is adequate contact between the electrode system and the biological site 12. If there is adequate contact the processor/controller 34 proceeds with ablation therapy by controlling the power generator 30 to output power. Based on the monitored power 32, the temperature data 22 and the flow-rate data 20 the processor/controller 34 adjusts the operation of the power generator 30.

The system 10 may further include one or more backplates 46. The backplate 46 is connected to the power generator 30 and provides a return path for the RF current delivered to the biological site 12 through the catheter system 16.

Figure 2:
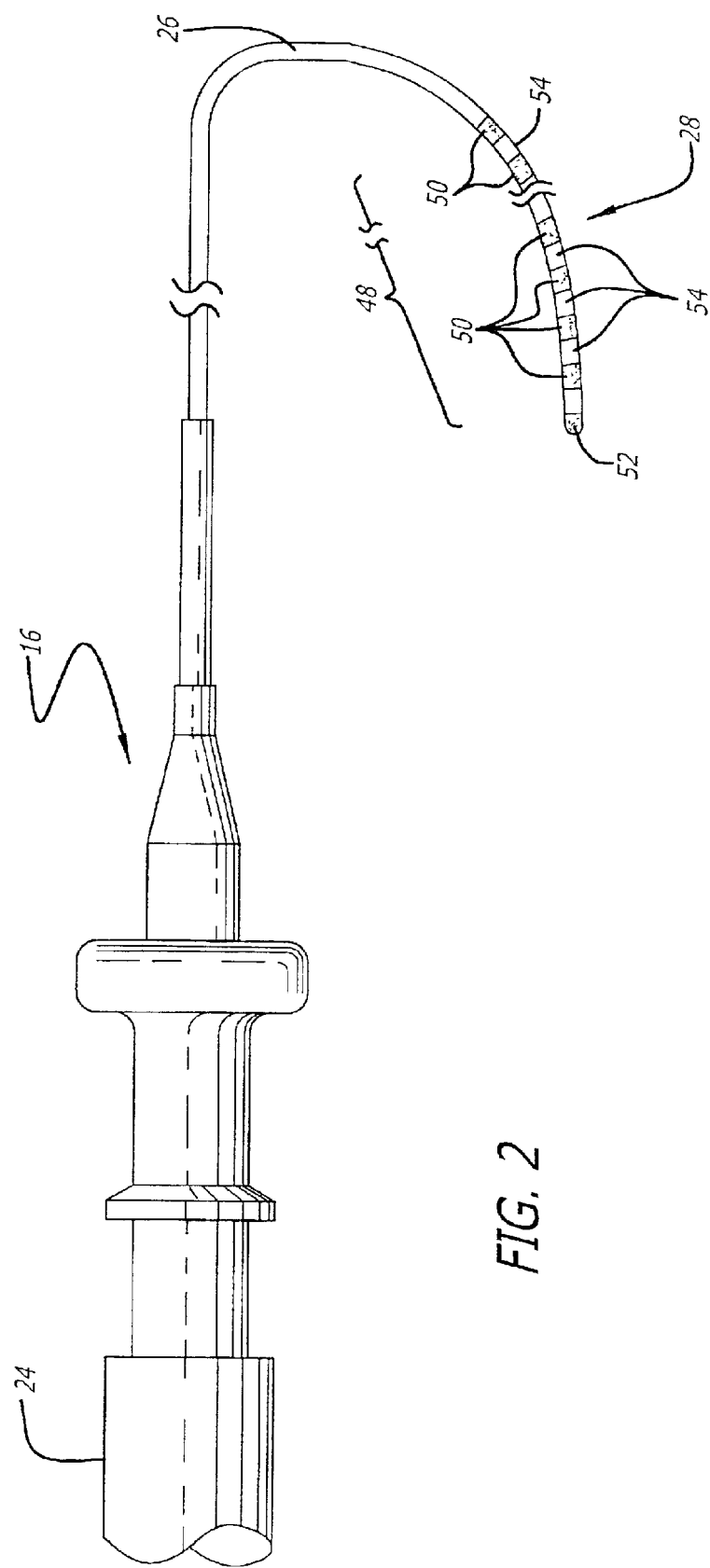
FIG. 2 is a diagram of the catheter system of FIG. 1 presenting more detail that includes a handle and a catheter sheath having a preformed distal segment carrying a linear array of electrodes.

As shown in FIG. 2, the distal segment 28 of the catheter system 16 includes an electrode system 48. A preferred embodiment of the electrode system 48 includes twelve band electrodes 50 arranged in a substantially linear array along the distal segment 28 of the catheter shaft 26. The electrode system 48 may include a tip electrode 52. (For clarity of illustration, only six band electrodes 50 are shown in FIG. 2 although as stated, a preferred embodiment may include many more.) The band electrodes 50 are arranged so that there is a nonconductive space 54 between adjacent electrodes. In one configuration of the electrode system 48, the width of the band electrodes 50 is 3 mm and the space 54 between the electrodes is 4 mm. The total length of the electrode system 48, as such, is approximately 8 cm.

The arrangement of the band electrodes 50 is not limited to a linear array and may take the form of other patterns. A substantially linear array is preferred for certain therapeutic procedures, such as treatment of atrial fibrillation, in which linear lesions of typically 4 to 8 cm in length are desired.

The band electrodes 50 are formed of a material having a significantly higher thermal conductivity than that of the biological tissue to be ablated. Possible materials include silver, gold, chromium, aluminum, molybdenum, tungsten, nickel, platinum, and platinum/10% iridium. Because of the difference in thermal conductivity between the band electrodes 50 and the tissue, the electrodes cool off more rapidly in the flowing fluids at the biological site. The band electrodes 50 are sized so that the surface area available for contact with fluid in the heart, e.g., blood, is sufficient to allow for efficient heat dissipation from the electrodes to the surrounding blood. In a preferred embodiment, the electrodes 50 are 7 French (2.3 mm in diameter) with a length of 3 mm.

Figure 3:
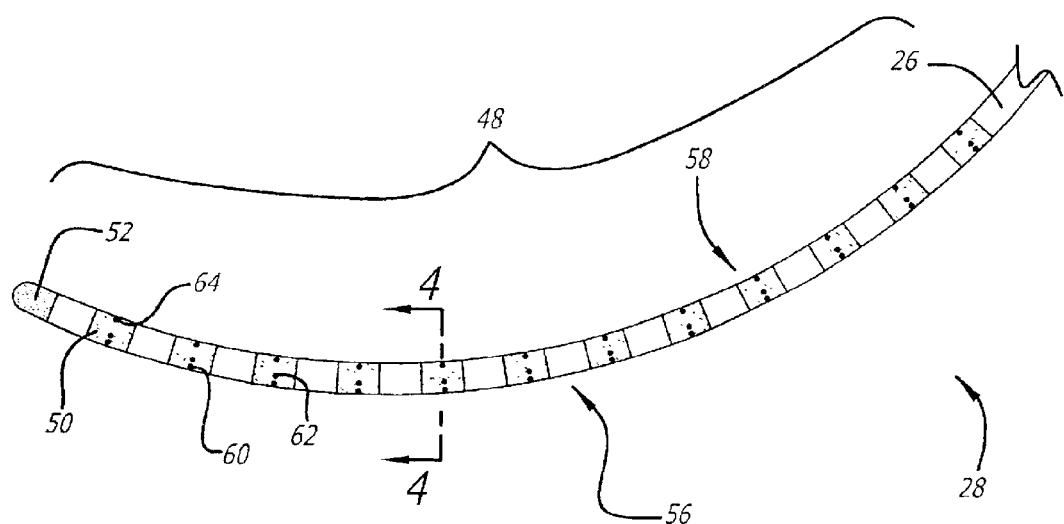
FIG. 3 is a diagram of the distal segment of the catheter system of FIG. 2 showing a plurality of pressure sensors, flow senors and thermal sensors located on a plurality of band electrodes.

As shown in FIG. 3, the distal segment 28 of the deflected catheter shaft 26 has an outside surface 56 and an inside surface 58. During ablation procedures, it is intended that the outside surface 56 contact the biological tissue undergoing ablation and that the inside surface 58 be in the blood pool. With continued reference to FIG. 3, in one configuration of the electrode system 48 a plurality of sensors are positioned at various points along the length of the distal segment 28. A plurality of pressure sensors 60 and thermal sensors 62 are located along the outside, tissue-contacting surface 56 while a plurality of flow sensors 64 are located along the inside surface 58 thereby placing them within the blood pool. The sensors 60, 62, 64 may be located in or on the electrodes 50 as shown in FIG. 3. In some configurations of the electrode system 48 each electrode 50 has at least one pressure sensor 60, flow sensor 64 and temperature sensor 62. In other configurations, sensors may be located on less than all of the electrodes. For example, the electrode system 48 maybe configured such that flow sensors 64 and pressure sensors 60 are located on every other electrode while temperature sensors 62 are located on every electrode.

Figure 4:
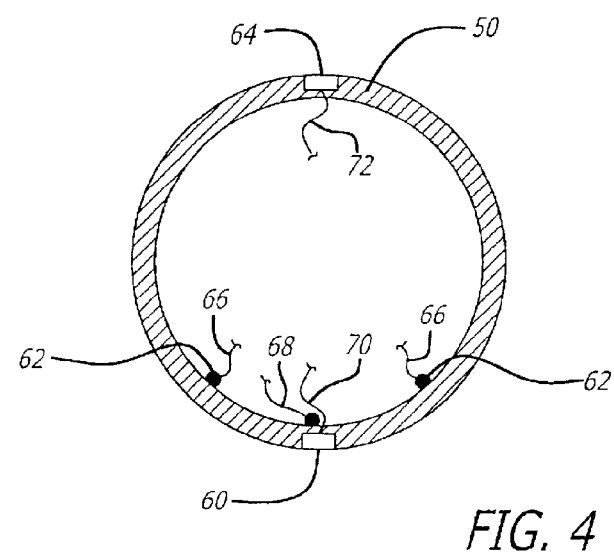
FIG. 4 is a cross-sectional view of the distal segment of FIG. 3 taken along line 4—4, depicting the positions of a pressure sensor, a flow sensor and two thermal sensors.

With reference to FIG. 4, in one embodiment of the electrode system, a pressure sensor 60 is positioned between a pair of thermal sensors 62 which are approximately 60 degrees apart along the circumference of the electrode while a flow sensor 64 is positioned opposite the pressure sensor 60. In a preferred embodiment, the two thermal sensors 62 are thermocouples formed using two temperature leads 66 and one power lead 68 such as described in U.S. Pat. No. 6,042,580, the disclosure of which is hereby incorporated by reference. In alternate embodiments, the thermal sensors 62 may include thermistors, resistance temperature detectors (RTD) and fluoroptic probes.

The flow sensor 64 may be any device capable of sensing the flow of fluid and providing an electrical signal based on the sensation of fluid flow. In one embodiment of the invention, the flow sensor 64 is an anemometer, preferably a hot wire anemometer comprising three perpendicular 500 $\mu$m×5 $\mu$m×2 $\mu$m polysilicon hot-wires that provide fluid flow measurements with time constants in the range of 120 and 330 $\mu$seconds, such as described in "Three dimensional silicon triple-hot-wire anemometer based on polymide joints", Thorbjorn Ebefors, Edvard Kalvesten, and Goran Stemme, IEEE Int. workshop on Micro Electro Machined System (MEMS 1998), Heidelberg, Germany, Jan. 25–29, 1998. In other embodiments, the flow sensor 64 may be the feedback from a Doppler ultrasound machine such as those manufactured by Acuson (models Sequoia and Apsen).

The pressure sensor 60 may be either a MEMS sensor or a piezo-electric transducer embedded in the outside surface of the electrode 50. The pressure sensor lead 70 passes through the electrode 50 and is fed through the shaft 26 to the proximal end of the catheter handle along with the temperature leads 66 and the power lead 68. The flow sensor 64 may be a MEMS sensor. It too has a lead 72 that passes through the electrode 50 and shaft 26.

Figure 5:
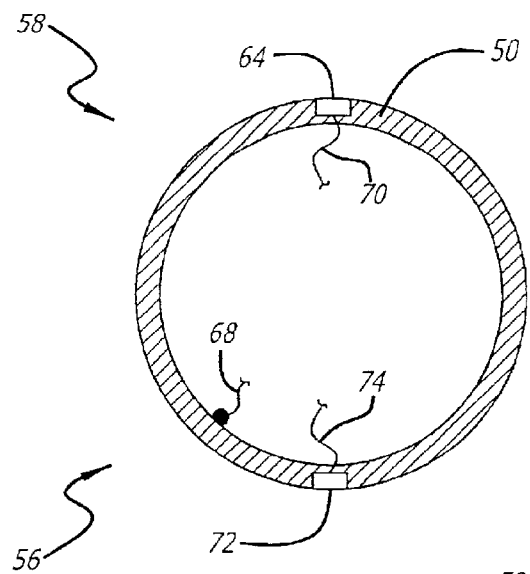
FIG. 5 is an alternate cross-sectional view of the distal segment depicting the positions of a pressure sensor, a flow sensor and a thermal sensor.
Figure 6:
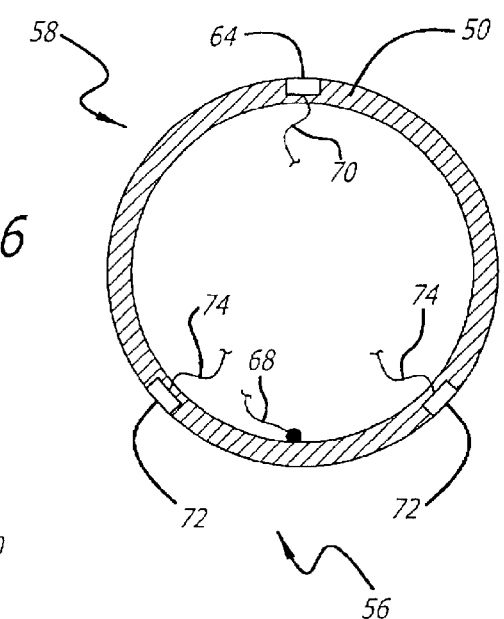
FIG. 6 is an alternate cross-sectional view of the distal segment depicting the positions of two pressure sensors, a flow sensor and a thermal sensor.
Figure 7:
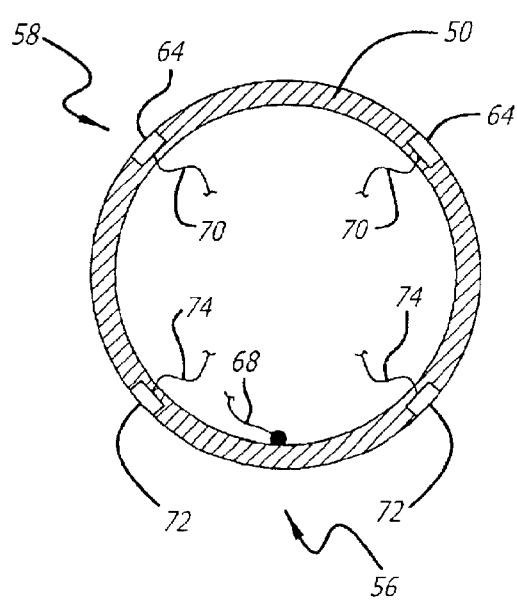
FIG. 7 is an alternate cross-sectional view of the distal segment depicting the positions of two pressure sensors, two flow sensors and a thermal sensor.

With reference to FIGS. 5, 6, and 7, in other embodiments, one or more combination pressure/temperature sensors 72 are positioned on the tissue-contacting side 56 of the electrode while one or more flow sensors 64 are positioned on the fluid-contacting side 58. In a preferred embodiment, the pressure/temperature sensor(s) 72 and the flow sensor(s) 64 are MEMS sensors. The pressure/temperature sensor lead(s) 74 and flow sensor lead(s) 70 pass through the electrode 50 and are fed through the shaft 26 to the proximal end of the catheter handle along with the power lead 68.

Figure 8:
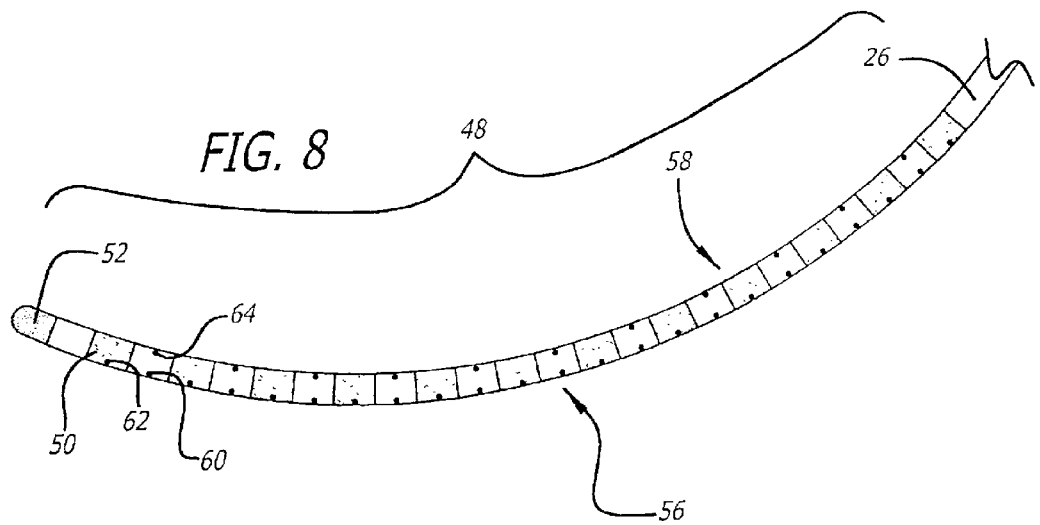
FIG. 8 is a diagram of an alternate configuration of the distal end segment of the catheter system of FIG. 2 showing a plurality of pressure sensors and flow senors located on the catheter shaft between adjacent band electrodes and a plurality of thermal sensors located on the band electrodes.

In an alternate configuration, as shown in FIG. 8, some or all of the pressure sensors 60 and flow sensors 64 may be located on the catheter shaft 26 between pairs of adjacent electrodes 50. In the multiple sensor embodiments thus described, each of the electrodes 50 has pressure sensor 60 and a flow sensor 64 associated with it and the energy applied to each electrode is individually controlled based on the information provided by the sensors.

Figure 9:
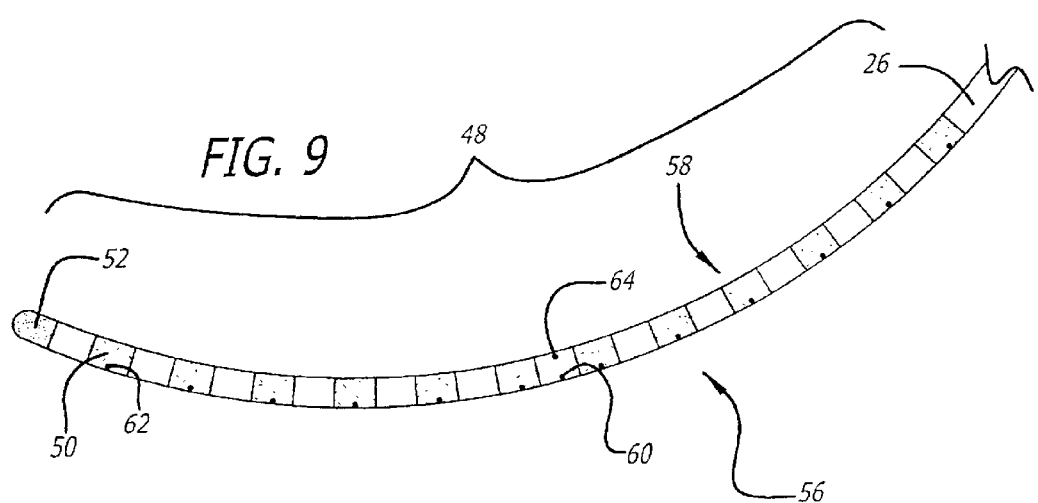
FIG. 9 is a diagram of an alternate configuration of the distal end segment of the catheter system of FIG. 2 showing a single pressure sensor and a single flow sensor positioned at the longitudinal center of the linear array of band electrodes and a plurality of thermal sensors located on the band electrodes.

In another configuration, as shown in FIG. 9, a single pressure sensor 60 and a single flow sensor 64 are positioned near the center of the electrode system 48, between a pair of adjacent band electrodes 50. In this arrangement, the pressure sensor 60 and the flow sensor 64 are located between the two middle electrodes 50 such that the pressure measurement and the biological fluid flow measurement are representative of the pressure and the flow rate along the entire electrode system 48. In this single sensor embodiment, the flow sensor 64 provides flow-rate data 20 (FIG. 1) and the pressure sensor 60 provides pressure data 18 to the processor/controller 34 that is used to control the energy application to each band electrode 50 within the electrode system 48.

Figure 10:
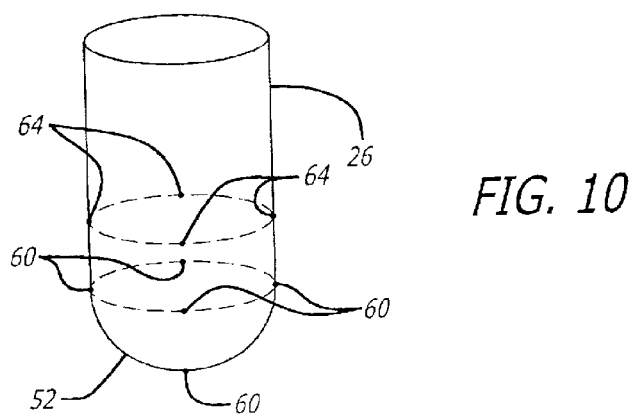
FIG. 10 is a schematic diagram of the tip electrode of the catheter system of FIG. 2 showing a plurality of flow sensors and pressure sensors positioned around the perimeter of the electrode.

In other catheter systems with tip ablating electrodes, such as shown in FIG. 10, one or more flow sensors 64 and pressure sensors 60 may be associated with the tip electrode 52. The sensors 60, 64 are embedded near or on the surface of the electrode 52. In the case of multiple flow sensors 64, the processor/controller 34 may control the application of energy based on the lowest of all flow rates measured or possibly the average flow rate. Likewise, in the case of multiple pressure sensors 60, the processor/controller 34 may control the application of energy based on the lowest of all pressures measured or possibly the average pressure.

Figure 11A:
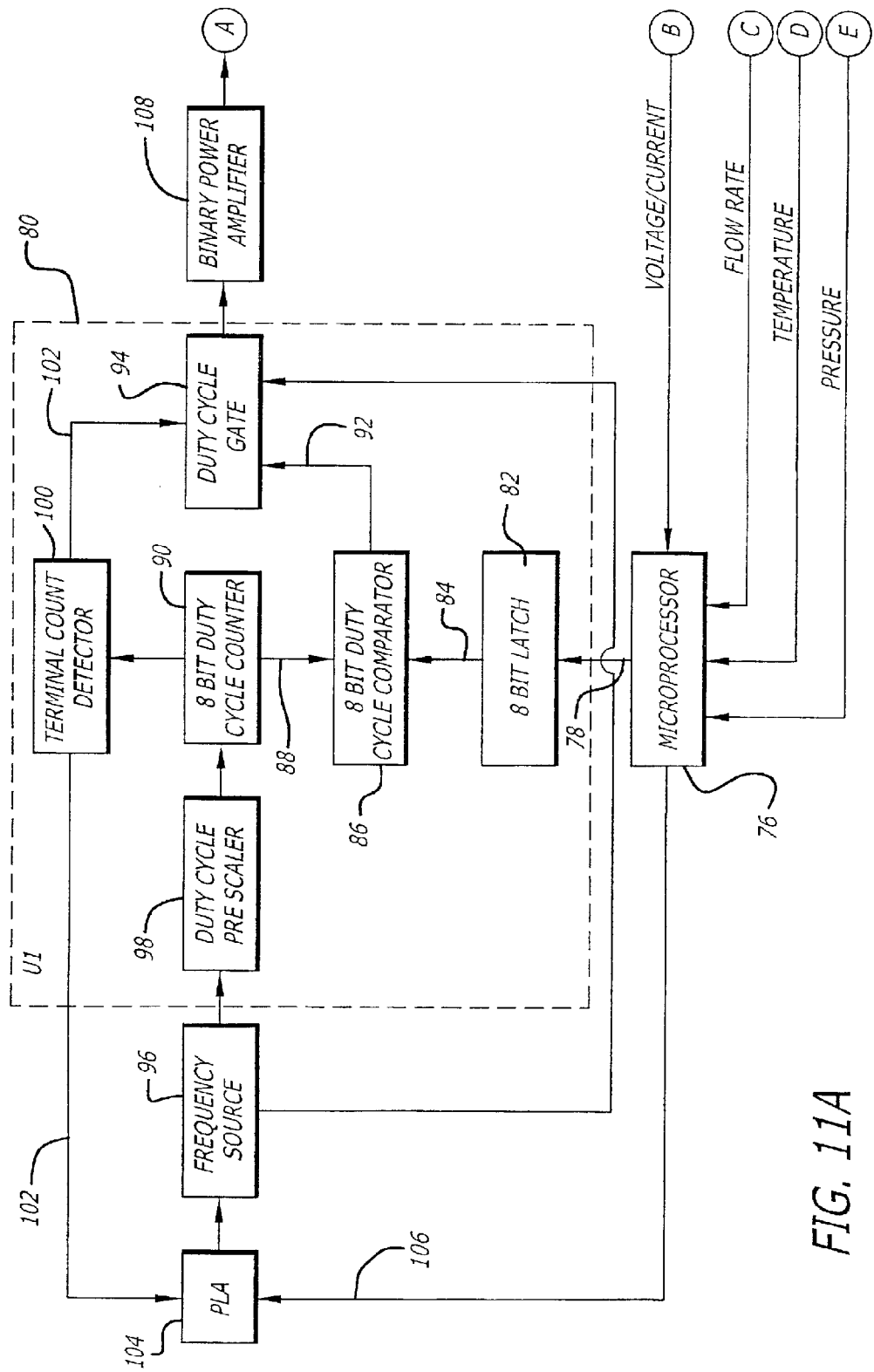

With reference to FIGS. 11A and 11B, there is shown a block diagram of an ablation system which incorporates aspects of the invention. In FIG. 11A, a microprocessor 76, which is part of the processor/controller 34 (FIG. 1), provides a duty cycle control signal 78 to a duty cycle generator ("DCG") 80. In this case, the duty cycle generator 80 receives the control signal 78 by an 8-bit latch 82. The latch 82 provides an 8-bit signal 84 to a duty cycle comparator 86. The comparator 86 compares the 8-bit signal 84 to a count 88 from an 8-bit duty cycle counter 90 and if the count is the same, provides a duty cycle off signal 92 to the duty cycle gate 94. The gate 94 is connected to a frequency source ("FS") 96, such as an oscillator that produces a 500 kHz signal. When the gate 94 receives the duty cycle off signal 92 from the comparator 86, it stops its output of the frequency source signal through the gate and no output exists.

At a frequency of 500 kHz, an 8-bit control has a period or time frame of 0.5 msec. At a fifty-percent duty cycle, the electrode is in the off period only 0.25 msec. The period or time frame is lengthened by use of a prescalar 98 interposed between the frequency source 96 and the counter 90. In one embodiment, the prescalar 98 lengthens the period to 4 msec thus allowing for a 2 msec off period during a fifty-percent duty cycle. Other lengths of the period may be used depending on the circumstances. It has been found that a ten percent duty cycle is particularly effective in ablating heart tissue.

A terminal count detector 100 detects the last count of the period and sends a terminal count signal 102 to the gate 94 which resets the gate for continued output of the frequency source signal. This then begins the on period of the duty cycle and the counter 90 begins its count again. In one preferred embodiment, the duty cycle is set at fifty percent and the 8-bit latch is accordingly set to 128. In another embodiment, the duty cycle is set at ten percent.

A programmable logic array ("PLA") 104 receives phase control signals 106 from the microprocessor 76 and controls the phase of the frequency source 96 accordingly. In one embodiment, the PLA 104 receives the terminal count signal 102 from the terminal count detector 100 and only permits phase changes after receiving that terminal count signal.

The output signal from the gate 94 during the on-period of the duty cycle is provided to a binary power amplifier ("BPA") 108 that increases the signal to a higher level, in this case, 24 volts. The amplified signals are then filtered with a band pass filter ("BPF") 110 to convert the somewhat square wave to a sine wave. The band pass filter 110 in one embodiment is centered at 500 kHz. The filtered signal is then provided to an isolated output transformer ("IOT") 112 that amplifies the signal to a much higher level, for example 350 volts peak-to-peak. This signal is then sent to a relay interconnect ("RI") 114 before it is provided as a power output signal OUTn 32 to the electrode 50.

In the embodiment shown in FIGS. 11A and 11B, a voltage and current monitor ("VCM") 116 is used to provide a power signal 118 to the microprocessor 76. The power signal 118 is indicative of the voltage and current of the power 32. As previously mentioned, some or all of the electrodes 50 may include one or more thermal sensors 62, a flow sensor 64 and a pressure sensor 60. The thermal sensor 62 provides temperature signals 22 which are used to determine the temperature at the electrode 50 while the pressure sensor 60 and flow sensor 64 provide pressure signals 18 and flow signals 20. The signals 18, 20, 22 and 118 are converted to digital form by an analog-to-digital converter within the microprocessor 76.

Figure 12A:
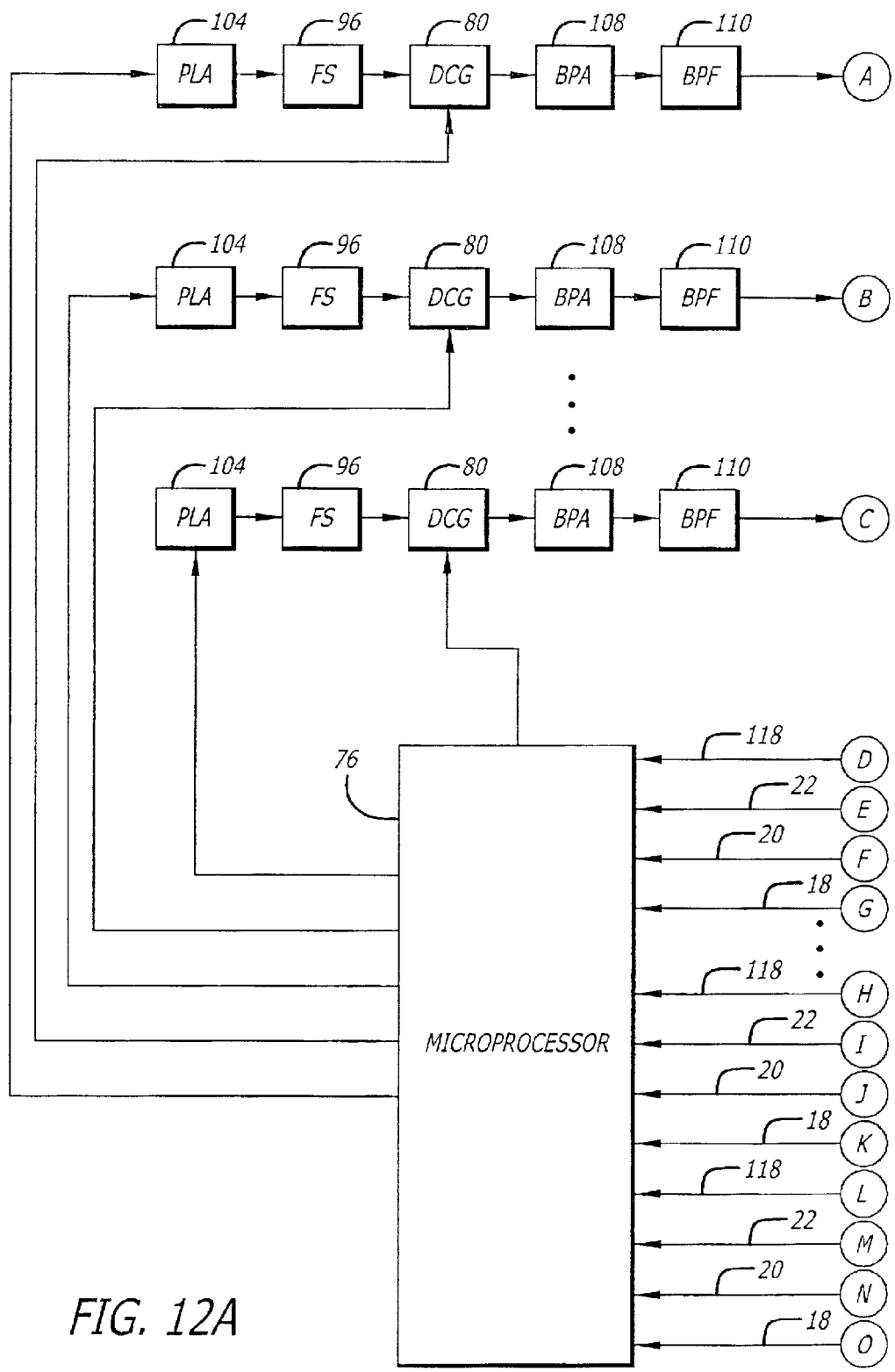
FIGS. 12A and 12B form a block diagram of a multichannel ablation system configured in accordance with the configuration of FIGS. 11A and 11B wherein a single PCS microprocessor controls the application of ablation energy to each channel individually.
Figure 12B:
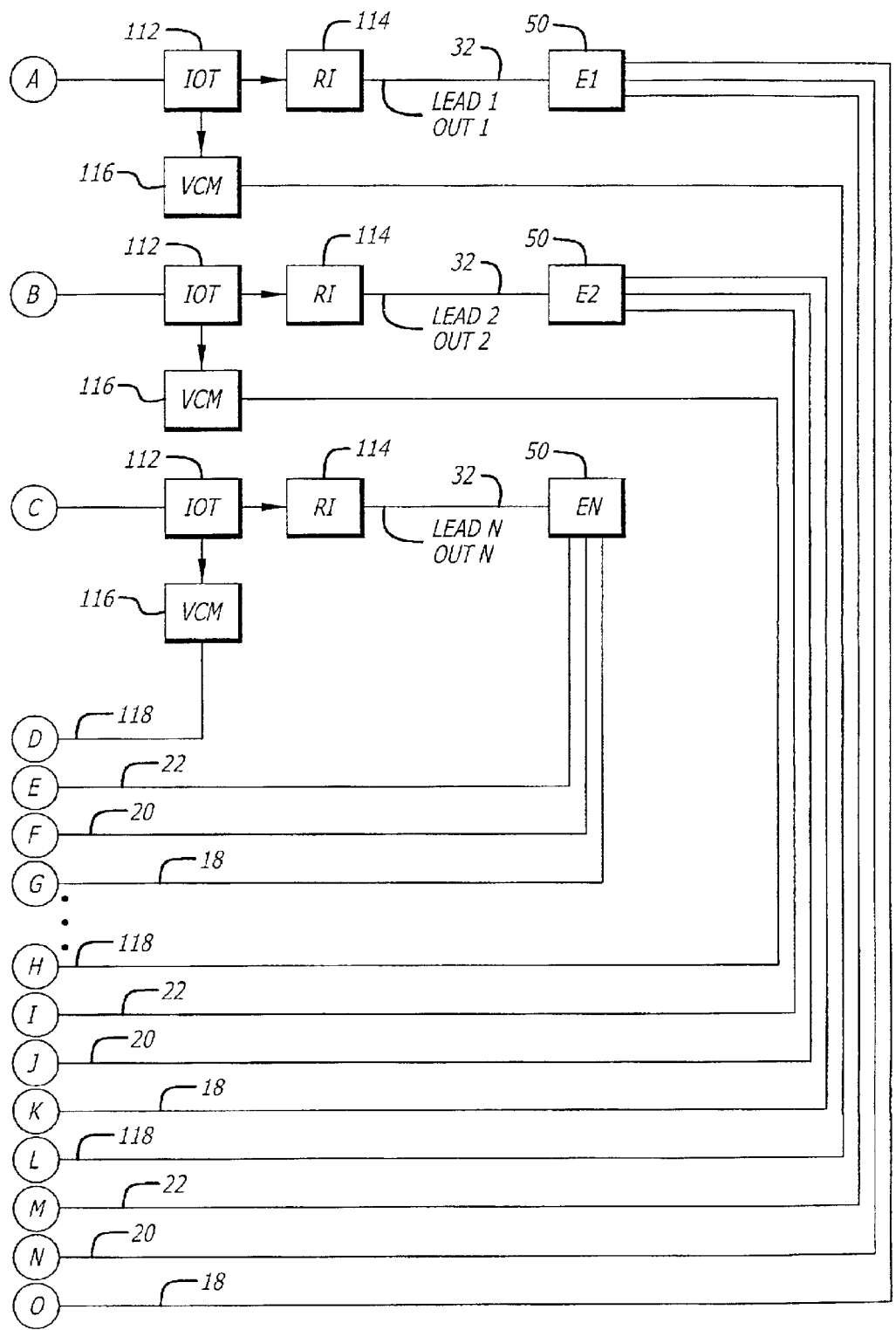

Referring now to FIGS. 12A and 12B, a block diagram of a multi-channel ablation system with thermal sensors, pressure sensors and flow sensors for use with a catheter system having a plurality of electrodes 50 is shown. The sensors are not depicted in the diagram but are understood to be closely associated with the electrodes 50 in that they are either on or near the electrodes. Although only three complete channels are shown, the system comprises many more as indicated by the successive dots. Those channels are not shown in FIGS. 12A and 12B to preserve clarity of illustration.

The single microprocessor 76, which again is part of the processor/controller 34 (FIG. 1), controls the duty cycle and the phase of each channel individually in this embodiment. Each channel shown comprises the same elements and each channel produces its own power output signal 32 (OUT1, OUT2, through OUTn where "n" is the total number of channels) on respective electrode leads (LEAD 1, LEAD 2, through LEAD n where "n" is the total number of leads).

Figure 13A:
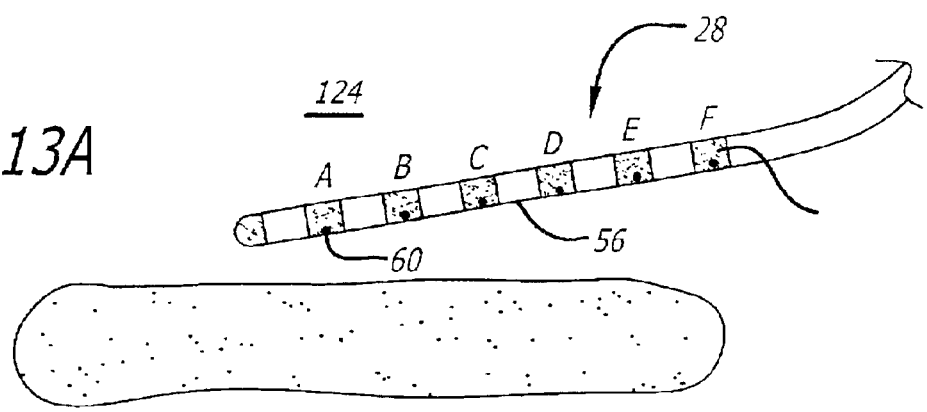
FIGS. 13A and 13B depict the distal segment of a catheter within a blood pool (FIG. 13A) and adjacent biological tissue (FIG. 13B)
Figure 13B:
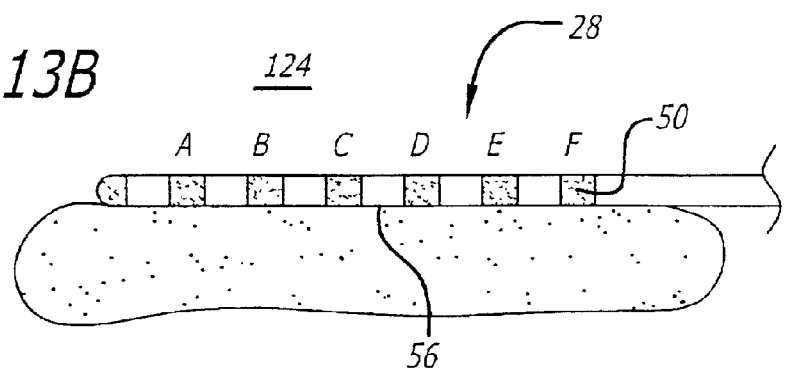

In operation, prior to the application of RF ablation energy, the ablation apparatus of the present invention provides for electrode/tissue contact assessment. With reference to FIGS. 13A and 13B, once the distal segment 28 is positioned within the biological site, e. g., the atrium of the heart, pressure data is collected and analyzed to determine the adequacy of electrode/tissue contact.

In one embodiment of the invention, the distal segment 28 is placed near or within the atrium and positioned under fluoroscopy such that the outside surface 56 lies within the local blood pool 124 thereby placing the pressure sensors 60 in the blood pool. Under microprocessor 76 control, one of the electrodes 50 in the blood pool 124 is selected to act as a reference electrode. For example, as shown in FIG. 13A, electrode C may be selected as the reference electrode. The pressure exerted on the reference electrode is measured. This pressure serves as a reference against which subsequent pressure measurements are compared to assess electrode/tissue contact.

Experimentation has shown that the pressure on electrodes placed within biological fluid, e. g., blood, are generally lower than the pressure on electrodes which contact biological tissue. With this as a guideline, once the reference pressure is determined, the distal segment 28 is repositioned, once again under fluoroscopy, such that the previously selected reference electrode, e.g. C, is positioned at a location perceived, under fluoroscopy, to be close to or in contact with tissue, as shown in FIG. 13B. The pressure on the electrode is measured. This new pressure measurement is referred to as an "assessment" pressure.

The assessment pressure and the reference pressure are then analyzed within the microprocessor. The differences between the assessment pressure and the reference pressure is monitored for variations which may be indicative of tissue contact. These differences may be based on a simple mathematical difference between the pressures or may be based on a percentage change in the pressure. Experimentation has shown that an assessment pressure increase, relative the reference pressure, of between 20% and 100% is indicative of electrode/tissue contact.

In a preferred embodiment, the microprocessor continuously calculates both reference and assessment pressures for a given period of time and determines the average pressure for each. This period of time may be, for example, 10 seconds. Contact assessment is then based on the average pressures. In using average values, the apparatus accounts for fluctuations in pressure values that may occur due to displacement of the electrodes caused by respiration and/or heart contractions.

The microprocessor analyzes the assessment pressure and the reference pressure and provides an indication of the state of the electrode/tissue contact. This indication may be provided on the front panel of the power control system through a display device. The display device may be in the form of a percentage indicative of the degree of confidence of electrode/tissue contact, with, for example, 100% indicating complete electrode/tissue contact and decreasing percentages indicating less electrode/tissue contact. Similar information may also be presented graphically by, for example, a bar graph.

The microprocessor calculates the percentage difference between the two pressures and provides the following indications. When the percentage difference is at least approximately 75% the microprocessor indicates that substantially complete electrode/tissue contact exists. The larger the percentage difference, the greater the level of confidence of electrode/tissue contact. When the percentage difference is in the approximate range between 20% and 75% the microprocessor indicates that partial electrode/tissue contact exists. When the percentage difference is less than approximately 20% the microprocessor indicates that there is no electrode/tissue contact.

With continued reference to FIGS. 13A and 13B, once the reference pressure of the local blood pool 124 is determined, an electrode/tissue contact assessment of each electrode 50 in the linear array may occur. Beginning, for example, with electrode A and continuing in sequence though electrode F, the pressure exerted on each electrode 50 is measured and compared to the reference pressure to assess electrode/tissue contact adequacy.

As previously mentioned, the pressures are preferably measured continuously for a few seconds in order to obtain a meaningful pressure average. This average measurement effectively filtrates the pressure fluctuations induced by heart contraction and respiration. In another embodiment of the invention described next, these pressure fluctuations assist in electrode/tissue contact assessment.

Respiration and contractions of the heart tend to cause an electrode, which may be in contact with the heart tissue, to move away from the tissue. With this in mind, once the distal segment 28 is positioned proximal biological tissue, a sequence of pressure measurements are taken over a time period sufficient to include several contradictions of the heart. Experimentation has shown that by monitoring these sequences for variations, an assessment of electrode/tissue contact may be made. The variation of pressures due to respiration/heart contraction is most noticeable when there is electrode tissue contact. Thus a large standard deviation from the average pressure may serve as an indicator of tissue contact. On the other hand, in analyzing the sample-to-sample variations in pressure caused by heart contractions it is noted that the value corresponding to blood pool placement has a smaller range of variations and thus a small standard deviation from the average pressure. A theory for this is that the catheter moves less simply because it is "floating" or not contacting tissue, and is less effected by respiration and by heart contraction.

The microprocessor analyzes the sequence of assessment pressures and provides an indication of the state of the electrode/tissue contact. The microprocessor first obtains an average pressure value based on a plurality of the pressure values. The microprocessor then calculates the standard deviation of the pressure values relative the average pressure. Next, the microprocessor calculates a deviation percentage by dividing the standard deviation by the average pressure and representing the result as a percentage value. The microprocessor then provides the following indications. When the deviation percentage is at least approximately 75% the microprocessor indicates that substantially complete electrode/tissue contact exists. The larger the deviation percentage, the greater the level of confidence of electrode/tissue contact. When the deviation percentage is in the approximate range between 20% and 75% the microprocessor indicates partial electrode/tissue contact exists. When the deviation percentage is less than approximately 20% the microprocessor indicates no electrode/tissue contact.

In one application of the apparatus in the right atrium, during tissue contact the average pressure during a 30 second time period was 20 grams while the standard deviation for the sequence of pressures was ±15. The deviation percentage was 75%. Without tissue contact, an average pressure of 10 grams with a standard deviation of ±2 was observed for the sequence of pressure values. The deviation percentage in this case was 20%. It is noted that when assessing contact based on a sequence of pressures it is not necessary to obtain a reference pressure, i.e., the pressure of the blood pool. Instead, the distal segment 28, may immediately be placed near the tissue and electrode/tissue contact assessment may be made.

Once adequate contact between the electrode system 48 and the biological tissue is confirmed, operation of the ablation system proceeds with power delivery. In this regard, the ablation system has two primary modes of power delivery: a constant power mode and an automatic temperature control mode.

Figure 14:
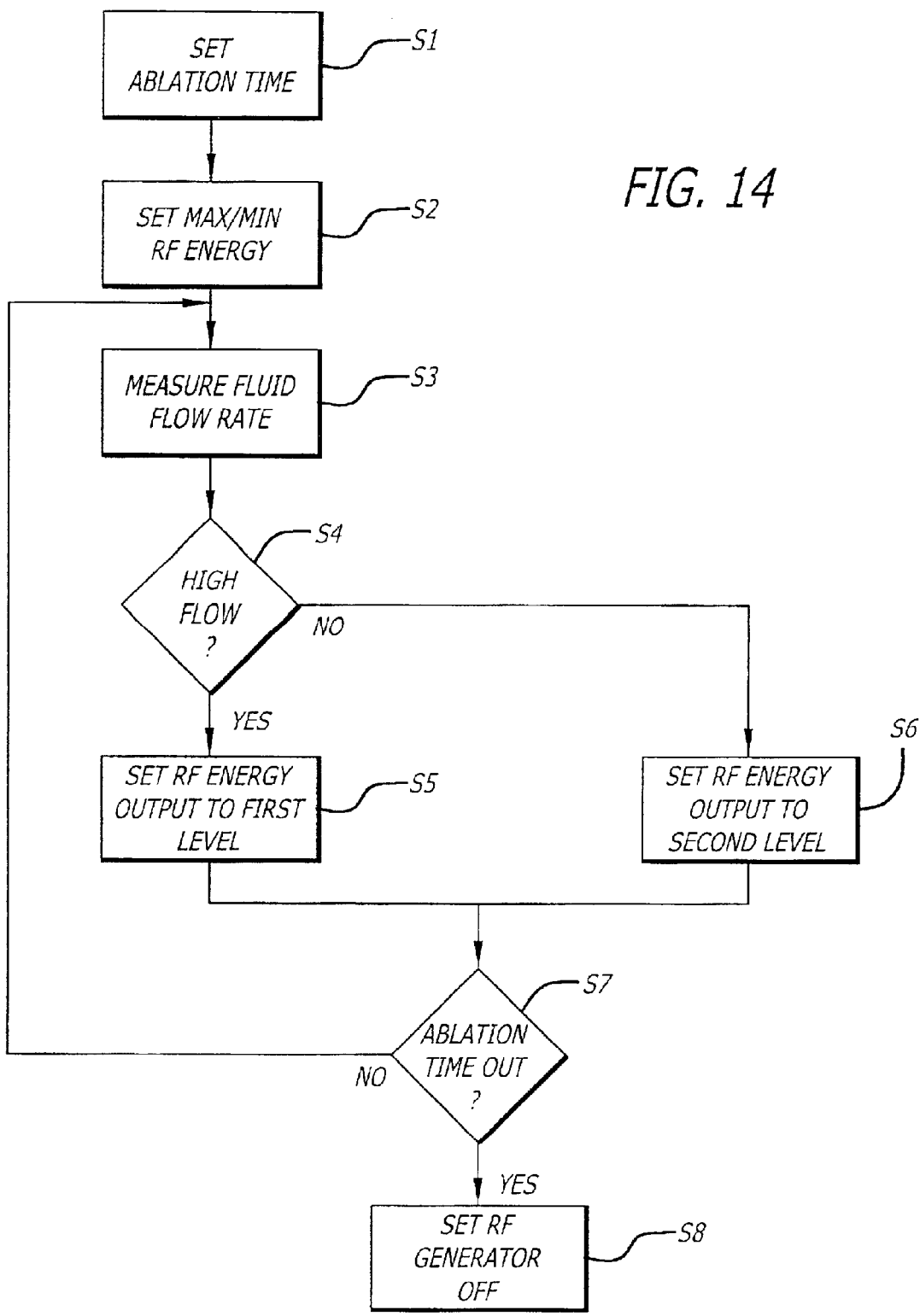
FIG. 14 is a flow chart of the operation of the ablation system when in a constant power mode.

With reference to FIG. 14, when operating in the constant power mode, at step S1, the user sets an ablation time and, at step S2 a maximum RF energy level value and a minimum RF energy level value which is less than the maximum value. These values are selected by the user based on various factors, including the biological site being ablated, the location of the ablation area within the biological site, the thermal, electrical and optical properties of the tissue being ablated and the desired characteristics of the ablation lesion desired, i.e., size and depth of lesion. The energy level and time values may be set through front panel controls on the RF generator.

At step S3, one or more flow sensors carried by the catheter measure the biological fluid-flow rate and send flow-rate-information signals to the microprocessor for analysis. The microprocessor is programmed to convert the flow-rate-information signals into fluid flow rate or fluid velocity values. The microprocessor is further programmed to identify the measured velocity values as being either "high" or "low." The microprocessor does this by comparing the measured velocity value to a predetermined velocity value. Measured velocity values greater than or equal to the predetermined velocity value are considered "high", while measured velocity values less than the predetermined velocity value are considered "low."

In one configuration, the flow rate of biological fluid through the site being treated is monitored using the flow rate sensors prior to ablation for a time period sufficient to identify a high-flow rate/low-flow rate pattern. The flow rate pattern is then analyzed by the microprocessor to identify high fluid flow and low fluid flow rates and to define the predetermined velocity value based on the high and low flow rates. For example, if the average high fluid flow rate within the time period is 30 cm/second and the average low fluid flow rate is 20 cm/second, the microprocessor may identify the predetermined velocity value as the average of the two, i. e., 25 cm/second. Thus periods during which the measured velocity value is greater than or equal to 25 cm/second would be considered high fluid-flow periods and those periods during which the measured velocity value is less than 25 cm/second would be considered low fluid-flow periods. Alternatively, the user may monitor the flow rate pattern and, using his personal judgment, manually program the predetermined velocity value into the microprocessor through front panel controls on the RF generator based. In an alternate configuration, the microprocessor may comprise a look up table that correlates user entered parameters with predetermined velocity values. Such parameter may include the biological site being ablated, the location of the ablation area within the biological site and the physical characteristics of the patient being treated.

At step S4, the microprocessor determines whether the flow rate is high or low. If the flow rate is high, at step S5 the microprocessor controls the output of RF energy from the RF generator such that RF energy of a first level is applied to the electrode. This first level of energy is substantially equal to the maximum RF energy level selected by the user. If the flow rate is low, at step S6 the microprocessor controls the output of RF energy from the RF generator such that RF energy of a second level is applied to the electrode. This second level of energy is substantially equal to the minimum RF energy level selected by the user and is usually at or near zero.

In the configuration of the RF generator described herein, the level of RF energy output is adjusted by controlling the duty cycle of the power. Increasing the duty cycle effects a corresponding increase in the energy output. Likewise, decreasing the duty cycle decreases the energy output. In alternate configurations of the RF generator, adjustments to energy outputs may be made by adjusting the amplitude of the power.

At step S7, the microprocessor determines whether the ablation time has expired. If the time has not expired, the operation process continues to measure the fluid-flow rate (step S3). If the ablation time has expired, the microprocessor sets the RF generator off at step S8.

Figure 15:
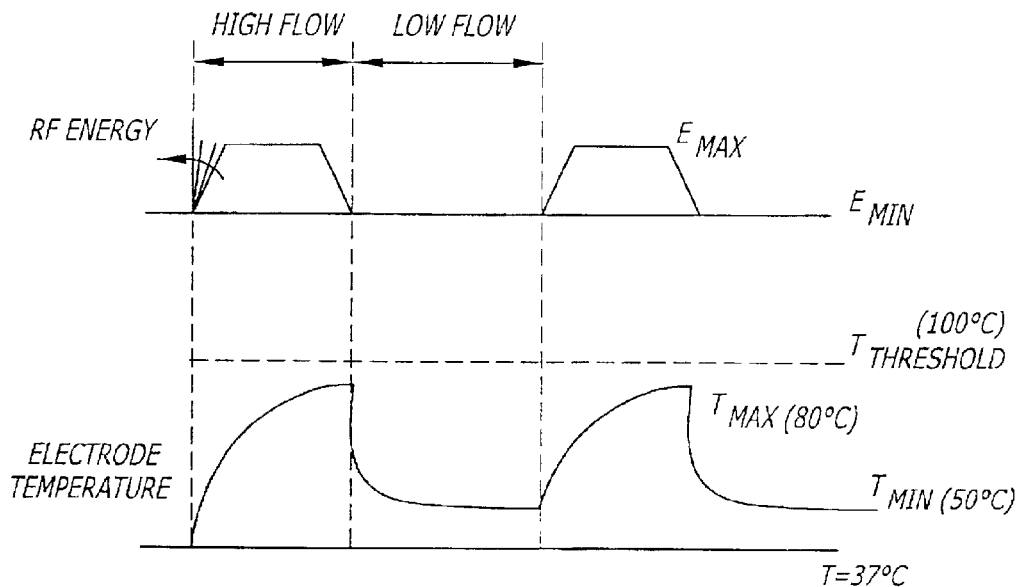
FIG. 15 is a graph depicting high-flow and low-flow periods, corresponding constant power RF energy applied during the periods and the resultant electrode temperature, each depicted as a function of time.

With reference to FIG. 15, as indicated by the electrode-temperature-verses-time curve, during high flow rate periods, when maximum RF energy is applied to the electrode, the temperature of the electrode approaches a target maximum temperature. As previously mentioned, the system provides temperature feedback signals to the microprocessor. The microprocessor monitors the temperature of the electrode and is adapted to ensure that the RF energy provided by the RF generator allows the electrode temperature to approach the target maximum temperature without exceeding a threshold maximum temperature. As a safeguard against exceeding a threshold maximum temperature for a period of time, the microprocessor shuts down the RF generator whenever the threshold maximum temperature is exceeded. The target temperature and threshold temperature may be programmed into the microprocessor through front panel controls. For ablation procedures performed in the heart, the target maximum temperature is preferably between approximately 50° C. and approximately 80° C. Because blood coagulation is known to occur at 100° C. the threshold maximum temperature is approximately 100° C. If the threshold maximum temperature is exceeded, the microprocessor shuts down the RF generator.

With continued reference to the electrode-temperature-verses-time curve of FIG. 15, during low flow rate periods, the minimum RF energy is applied to the electrode. As previously mentioned, minimum RF energy is less than the maximum RF energy and is generally at or near zero. With the RF energy at a substantially reduced level, the temperature of the electrode is able to approach a target minimum temperature, which is preferably 50° C. Again, the target minimum temperature may be entered into the microprocessor.

Figure 16:
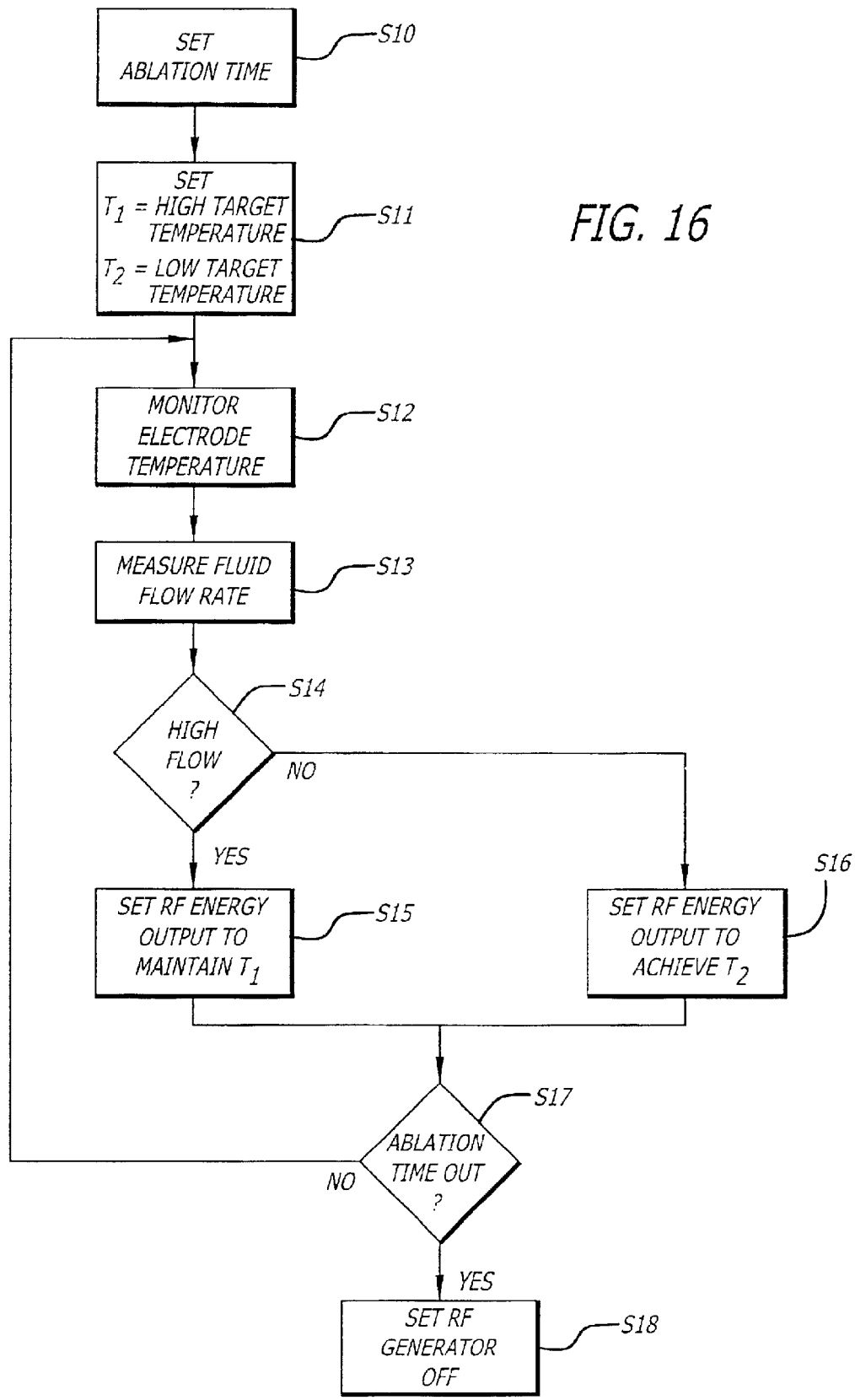
FIG. 16 is a flow chart of the operation of the ablation system when in the automatic temperature controlled mode.

With reference to FIG. 16, when operating in the automatic temperature control mode, at step S10, the user sets an ablation time and, at step S11 a high target temperature and a low target temperature. These values are selected by the user based on various factors, including the biological site being ablated, the location of the ablation area within the biological site, the thermal, electrical and optical properties of the tissue being ablated and the desired characteristics of the ablation lesion desired, i.e., size and depth of lesion. A typical high target temperature used for ablation procedures in the heart is between approximately 50° C. and approximately 80° C., while a typical low target temperature is between approximately 42° C. and approximately 50° C. The temperature and time values may be set through front panel controls of the RF generator.

At step S12, the microprocessor monitors the electrode temperature using the temperature feedback signals provided by the thermal sensor on the electrode. At step S13, one or more flow sensors carried by the catheter measure the biological fluid-flow rate and send flow-rate-information signals to the microprocessor for analysis.

At step S14 the microprocessor determines whether the actual measured flow rate is high or low. If the flow rate is high, at step S15 the microprocessor controls the output of RF energy from the RF generator such that the RF energy provided to the electrode allows the electrode temperature to approach the high target temperature, without exceeding a threshold maximum temperature, which is approximately 100° C. If the threshold maximum temperature is exceeded, the microprocessor shuts down the RF generator. If the flow rate is low, at steps S16 the microprocessor controls the output of RF energy from the RF generator such that RF energy provided to the electrode allows the electrode temperature to approach the low target temperature.

At step S17, the microprocessor determines whether the ablation time has expired. If the time has not expired, the operation process returns to step S12. If the ablation time has expired, the microprocessor sets the RF generator off at step S18.

Figure 17:
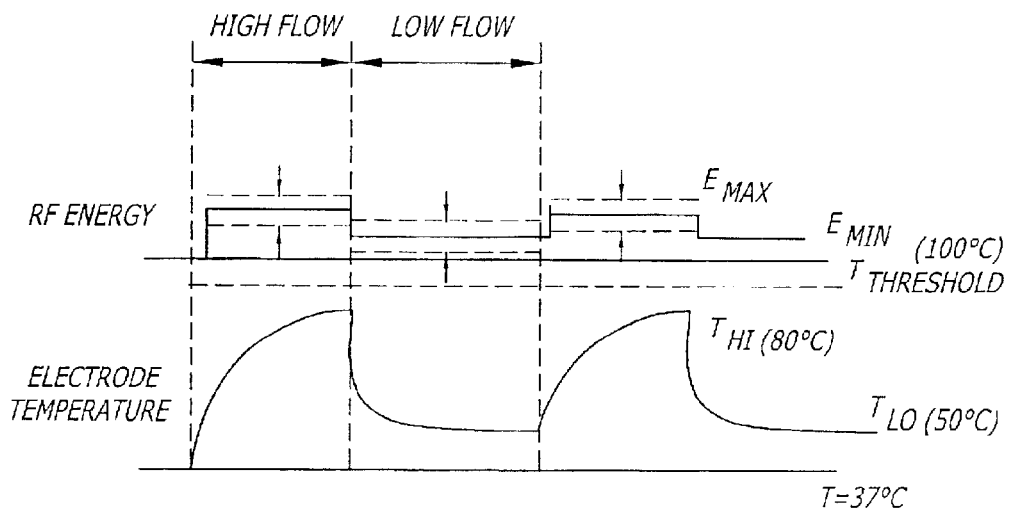
FIG. 17 is a graph depicting high-flow and low-flow periods, corresponding automatic temperature controlled RF energy applied during the periods and the resultant electrode temperature, each depicted as a function of time.

The microprocessor is programmed to identify "high" and "low" flow rates accordingly, in the manner as previously discussed with regard to the constant power mode operation. As shown in FIG. 17, at the beginning of a high flow rate period, the RF energy level is pulsed up from the minimum value, e.g., zero, to the maximum value which is greater than the minimum value. At the end of the high flow rate period, the RF energy is pulsed down to the minimum value. The energy remains at this level throughout the low flow rate period, until the start of the next high flow rate period, at which time the RF energy is again pulsed up to the maximum value.

As indicated by the electrode-temperature-verses-time curve, during high flow rate periods, when RF energy of a first level is applied to the electrode, the temperature of the electrode approaches the high target temperature. As previously mentioned, the system provides temperature feedback signals to the microprocessor. The microprocessor monitors the temperature of the electrode and is adapted to control the RF generator such that the RF energy provided by the RF generator allows the electrode temperature to approach the high target temperature without exceeding the threshold maximum temperature. If the high target temperature is not reached during the first high fluid-flow period, the microprocessor may incrementally increase the RF energy during subsequent high fluid-flow periods, as indicated by the dashed lines on the RF energy graph, until the high target temperature is reached. Likewise, if the electrode temperature exceeds the high target temperature but is less than the threshold maximum temperature, the microprocessor may incrementally decrease the RF energy during subsequent high fluid-flow periods. If the threshold maximum value is exceeded, the microprocessor shuts down the RF generator.

With continued reference to the electrode-temperature-verses-time curve of FIG. 17, during low flow rate periods, when RF energy of a second level is applied to the electrode, the temperature of the electrode approaches a low target temperature, which is preferably 50° C. If the temperature of the electrode does not decrease toward the low target temperature sufficiently fast, the microprocessor may incrementally decrease the RF energy during subsequent low fluid-flow periods, as indicated by the dashed lines in the RF energy graph, until the low target temperature is reached. Conversely, if at anytime during a low flow rate period the electrode temperature decreases to a level less than the low target temperature, the microprocessor may incrementally increase the RF energy during subsequent low fluid-flow periods to maintain the electrode temperature at or near the low target temperature.

In an alternate embodiment, also having a constant power mode and an automatic temperature control mode, the microprocessor is adapted to continuously monitor the fluid flow rate and to dynamically adjust the RF energy level provided by the generator by increasing or decreasing RF energy levels based on corresponding increases and decreases in fluid-flow rates.

Figure 18:
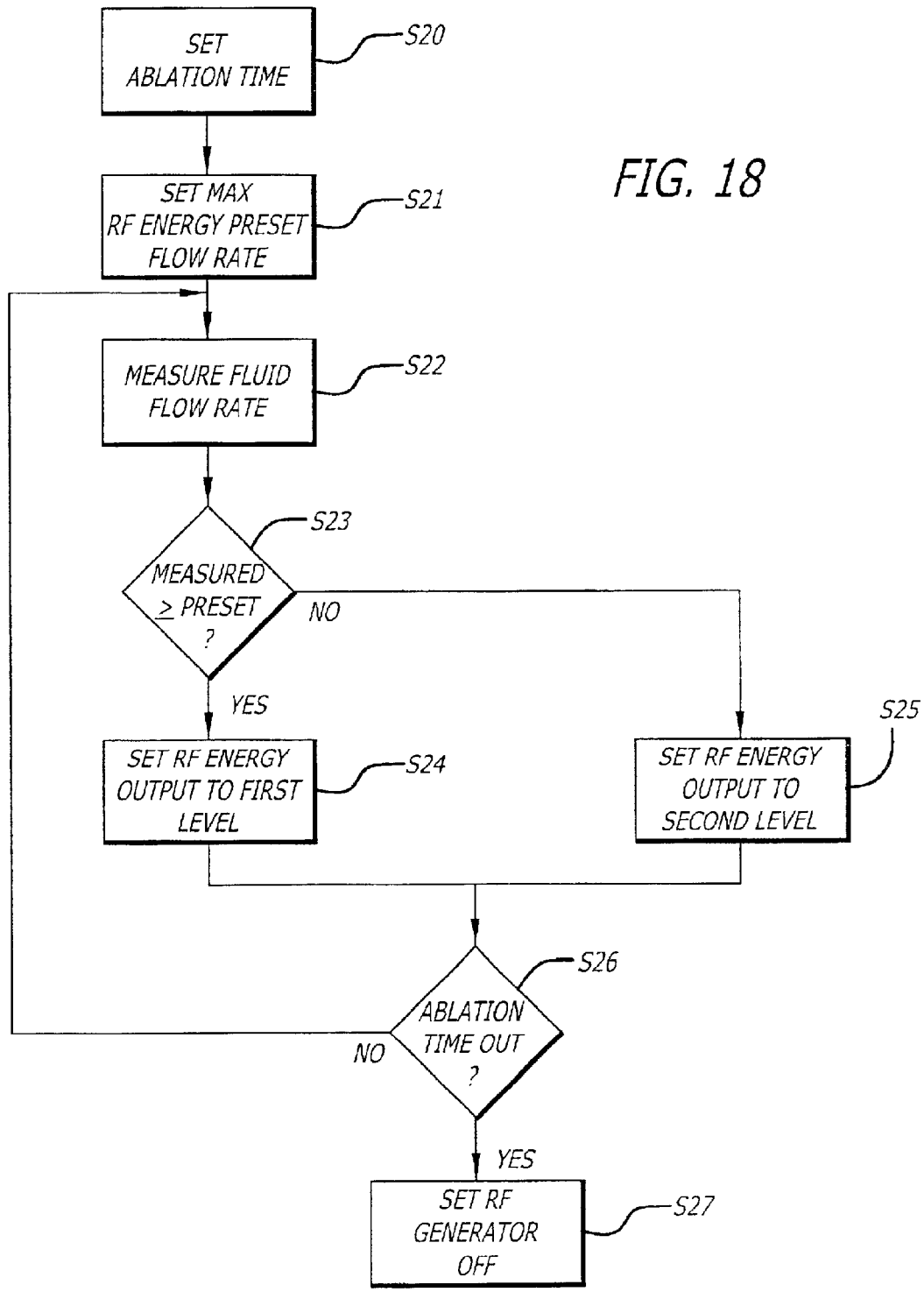
FIG. 18 is a flow chart of an alternate operation of the ablation system when in a constant power mode.

With reference to FIG. 18, when operating this alternate embodiment in the constant power mode, at step S20, the user sets an ablation time and, at step S21 a preset flow rate value and a maximum RF energy level value. These values may be selected and determined as described with reference to the previously discussed embodiments. The ablation time, preset flow rate value and maximum RF energy level value may be set through front panel controls of the RF generator.

At step S22, one or more flow sensors carried by the catheter measure the biological fluid-flow rate and send flow-rate-information signals to the microprocessor for analysis. At steps S23 the microprocessor determines whether the measured flow rate is greater than or equal to the preset flow rate value. If the measured flow rate is greater than or equal to the preset flow rate value, at step S24 the microprocessor controls the output of RF energy from the RF generator such that the maximum level of RF energy is applied to the electrode.

If the measured flow rate is less than the preset flow rate, at step S25 the microprocessor calculates a rate of reduction for the flow rate. This rate of reduction is calculated by comparing the measured flow rate to the preset flow rate. In a preferred embodiment, the ratio of the two flow rates provides the comparison necessary to determine the rate of reduction. Using the rate of reduction in the flow rate, the microprocessor determines a corresponding rate of reduction in the applied energy level. The correlation between reduction in the flow rate and the energy delivery rate can be a linear relationship, e.g., 1:1, 2:1, etc. Alternatively, the rate of decrease of energy delivery may be a polynomial of the inverse of the rate of flow decrease.

At step S26, the microprocessor determines whether the ablation time has expired. If the time has not expired, the operation process returns to step S22. If the ablation time has been expired, the microprocessor sets the RF generator off at step S27.

As with the previously discussed embodiments, the microprocessor monitors the temperature of the electrode and is adapted to ensure that the RF energy provided by the RF generator is allowed to approach the maximum RF energy without exceeding a threshold maximum temperature value. If the threshold maximum value is exceeded, the microprocessor shuts down the RF generator.

With reference to FIG. 19, when operating the alternate flow sensor embodiment in the automatic temperature control mode, at step S30, the user sets an ablation time and, at step S31, a high target temperature, a low target temperature, and a preset flow rate. The target temperatures are selected in a manner similar to that previously discussed with respect to FIG. 16, while the preset flow rate is selected in a manner similar to that previously discussed with regard to the other embodiments. The temperature, time, and preset flow rate value may be set through front panel controls of the RF generator.

At step S32, the microprocessor monitors the electrode temperature using the temperature feedback signals provided by the thermal sensor on the electrode. At step S33, one or more flow sensors carried by the catheter measure fluid-flow rate and send the flow-rate-information signals to the microprocessor, where they are processed and compared to the preset flow rate.

At steps S34 the microprocessor determines whether the measured flow rate is greater than or equal to the preset flow rate value. If the measured flow rate is greater than or equal to the preset flow rate value, at step S35 the microprocessor calculates a rate of increase for the flow rate. This rate of increase is calculated by comparing the measured flow rate to the preset flow rate. In a preferred embodiment, the ratio of the two flow rates provides the comparison necessary to determine the rate of increase. Using the rate of increase in the flow rate, the microprocessor determines a corresponding rate of increase in the applied energy level. The correlation between the increase in the flow rate and the energy delivery rate can be a linear relationship. Alternatively the rate of increase of energy delivery may be a polynomial of the inverse of the rate of flow increase.

During this process, the microprocessor monitors the temperature of the electrode. The microprocessor is adapted to control the RF generator such that the RF energy provided by the RF generator allows the electrode temperature to approach the high target temperature without exceeding the threshold maximum temperature. If the high target temperature is not obtained by the applied energy level, the microprocessor may increase the RF energy until the high target temperature is reached. Likewise, if the electrode temperature exceeds the high target temperature but is less than the threshold maximum temperature, the microprocessor may decrease the RF energy. If the threshold maximum value is exceeded, the microprocessor shuts down the RF generator.

At steps S36, if the microprocessor determines that the measured flow rate is less than the preset flow rate value, the microprocessor calculates a rate of reduction for the flow rate. This rate of reduction is calculated by comparing the measured flow rate to the preset flow rate. In a preferred embodiment, the ratio of the two flow rates provides the comparison necessary to determine the rate of reduction. Using the rate of reduction in the flow rate, the microprocessor determines a corresponding rate of reduction in the applied energy level. The correlation between reduction in the flow rate and the energy delivery rate can be a linear relationship. Alternatively, the rate of decrease of energy delivery maybe a polynomial of the inverse of the rate of flow decrease.

During this process, the microprocessor monitors the temperature of the electrode. If the temperature of the electrode does not decrease toward the low target temperature sufficiently fast, the microprocessor may decrease the RF energy, until the low target temperature is reached. Conversely, if at anytime during a low flow rate period the electrode temperature decreases to a level less than the low target temperature, the microprocessor may increase the RF energy to maintain the electrode temperature at or near the low target temperature.

At step S37, the microprocessor determines whether the ablation time has expired. If the time has not expired, the operation process returns to step S32. If the ablation time has expired, the microprocessor sets the RF generator off at step S38.

While the various embodiments of the invention have been described as using RF energy to effect ablation, the invention is not limited to this type of energy. Various other energy sources may be used such as microwave, ultrasound, laser and cyro sources.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A catheter for use during treatment of biological tissue within a biological organ having fluid flowing therethrough, said catheter comprising:
    a shaft having a distal segment adapted to be positioned in the biological organ, the distal segment having a tissue-contacting area and a fluid-contacting area spaced apart from the tissue-contacting area, wherein the space between the two areas allows for the tissue-contacting area to contact the biological tissue while the fluid-contacting area contacts the fluid flowing through the organ;
    at least one pressure sensor associated with the distal segment and positioned within the tissue-contacting area, the pressure sensor adapted to provide pressure data indicative of the pressure exerted on the distal segment at or near the pressure sensor; and
    at least one flow sensor positioned within the fluid-contacting area and adapted to provide flow-rate data indicative of the flow rate of the fluid through the biological organ.

2. The catheter of claim 1 further comprising an electrode system at the distal segment, the electrode system adapted to transmit energy to the biological tissue.

3. The catheter of claim 2 wherein the electrode system comprises at least one electrode and the at least one pressure sensor is located on the electrode.

4. The catheter of claim 2 wherein the electrode system comprises at least one electrode and the at least one pressure sensor is located on the shaft adjacent the electrode.

5. The catheter of claim 2 wherein the electrode system comprises a plurality of band electrodes, a plurality of which have a pressure sensor associated therewith.

6. The catheter of claim 5 wherein the pressure sensors are located on the band electrodes.

7. The catheter of claim 5 wherein the pressure sensors are located on the shaft between adjacent band electrodes.

8. The catheter of claim 2 wherein the electrode system comprises a plurality of band electrodes arranged in a linear array and the at least one pressure sensor is located on the shaft near the longitudinal center of the array.

9. The catheter of claim 2 wherein the electrode system comprises a plurality of band electrodes, a plurality of which have a flow sensor associated therewith.

10. The catheter of claim 9 wherein the flow sensors are located on the band electrodes.

11. The catheter of claim 9 wherein the flow sensors are located on the shaft between adjacent band electrodes.

12. The catheter of claim 2 wherein the electrode system comprises a plurality of band electrodes arranged in a linear array and the at least one flow sensor is located on the shaft near the longitudinal center of the array.

13. The catheter of claim 1 further comprising at least one temperature sensor associated with the distal segment and positioned within the tissue-contacting area, the temperature sensor adapted to provide temperature data indicative of the temperature at the interface between the temperature sensor and the tissue.

14. The catheter of claim 13 further comprising an electrode system at the distal segment, wherein the electrode system comprises at least one electrode and the at least one temperature sensor is located on the electrode.

15. The catheter of claim 13 further comprising an electrode system at the distal segment, wherein the electrode system comprises a plurality of band electrodes, a plurality of which have at least one temperature sensor located thereon.

16. A system for applying energy to biological tissue within a biological organ having fluid flowing therethrough, said system comprising:
    a generator for providing energy;
    a catheter carrying an electrode system at its distal segment, the distal segment having a tissue-contacting area adapted to be positioned in the biological organ and intended to contact the biological tissue, and the electrode system adapted to receive energy from the generator;
    at least one pressure sensor associated with the distal segment, located within the tissue-contacting area and adapted to provide pressure data indicative of the pressure exerted on the distal segment at or near the pressure sensor; and a processor responsive to the pressure data and configured to analyze the pressure data and provide an indication of contact between the distal segment at or near the pressure sensor and the tissue, wherein the indication comprises a visual display of a degree of electrode/tissue contact.

17. The system of claim 16 wherein the processor is adapted to:

convert the pressure data to a measured pressure value;

compare the measured pressure value to a reference pressure value indicative of adequate contact between the distal segment at or near the pressure sensor and the tissue; and provide an indication or adequate contact when the measured pressure value is at least as great as the reference pressure value.

18. The system of claim 16 wherein the processor is adapted to:

convert the pressure data to a measured pressure value;

determine the percentage difference between a reference pressure value and the measured pressure value, the reference pressure value indicative of the pressure on the distal segment at or near the pressure sensor when the distal segment positioned in the biological fluid; and compare the percentage difference to a plurality of predetermined contact assessment criteria and provide an indication result, the criteria and results comprising, for a percentage difference of at least approximately 75%, indicating substantially complete contact, for a percentage difference in the approximate range between 25% and 75%, indicating partial contact, and for a percentage difference less than approximately 20%, indicating no contact.

19. The system of claim 16 wherein the pressure data comprises a sequence of pressure values indicative of the pressure on the distal segment over a period of time and the processor is adapted to monitor the sequence of pressure values for variations indicative of contact between the distal segment at or near the pressure sensor and the tissue.

20. The system of claim 19 wherein the processor is adapted to:

determine an average pressure value based on the sequence of pressure values;

calculate the standard deviation of the pressure values relative the average pressure;

calculate a deviation percentage;

compare the deviation percentage to a plurality of predetermined contact assessment criteria; and provide an indication result, the criteria and results comprising, for a deviation percentage at least approximately 75%, indicating substantially complete contact, for a deviation percentage in the approximate range between 20% and 75%, indicating partial contact; and for a standard deviation percentage less than approximately 20%, indicating no contact.

21. The system of claim 16 wherein:

the distal segment has a fluid-contacting area intended to contact the fluid and the system further comprises at least one flow sensor positioned within the fluid-contacting area and adapted to provide flow-rate data indicative of the flow rate of the fluid through the biological organ; and the processor is adapted to receive the flow rate information, process the flow rate information to assess whether the fluid-flow rate is high or low and control the generator such that the generator provides energy of a first level to the electrode system during periods of high fluid-flow and energy of a second level, less than the first level, during periods of low fluid-flow.

22. The system of claim 21 wherein the processor is adapted to control the generator to increase the energy level to the first energy level at the beginning of the high flow period and to decrease the energy level to the second energy level toward the end of the high flow period and before the beginning of the next low flow period.

23. The system of claim 16 wherein:

the distal segment has a fluid-contacting area intended to contact the fluid and the system further comprises at least one flow sensor positioned within the fluid-contacting area and adapted to provide flow-rate data indicative of the flow rate of the fluid through the biological organ; and the processor is adapted to control the generator such that the generator provides energy to the electrode system based on the flow-rate data.

24. The system of claim 23 wherein a preset flow rate and a maximum energy level are programmed into the processor and the processor is adapted to:

compare the measured flow rate to the preset flow rate;

set the provided energy level to the maximum energy level when the measured flow rate is greater than or equal to the preset flow rate; and determine the rate of reduction of the measured flow rate relative to the preset flow rate and set the provided energy level to a value less than the maximum energy level, the provided level being a multiple of the maximum energy level, the multiple being set based on the determined reduction rate when the measured flow rate is less than the preset flow rate.

25. The system of claim 16 further comprising:

a temperature sensor adapted to provide temperature signals to the processor, the signals indicative of the temperature at the electrode system;

wherein the processor is adapted to determine the temperature at the electrode system based on the temperature signals and to control the generator such that the level of energy applied to the electrode system maintains the temperature of the electrode system at or near a target temperature.

26. A system for assessing the adequacy of contact between an electrode and biological tissue within a biological organ having biological fluid therein, said system comprising:

a pressure sensor configured to provide a reference pressure indicative of the pressure at the electrode when the electrode is positioned in the biological fluid and configured to provide an assessment pressure indicative of the pressure at the electrode when the electrode is positioned proximal the biological tissue; and a processor responsive to the reference and assessment pressure signals and configured to analyze the pressure signals and indicate the state of electrode/tissue contact, wherein the indication comprises a visual display of a degree of electrode/tissue contact.

27. The system of claim 26 wherein the processor is adapted to:

determine the percentage difference between the reference pressure and the assessment pressure; and compare the percentage difference to a plurality of predetermined contact assessment criteria and provide an indication result, the criteria and results comprising, for a percentage difference of at least approximately 75%, indicating substantially complete electrode/tissue contact, for a percentage difference in the approximate range between 20% and 75%, indicating partial electrode/tissue contact, and for a percentage difference less than approximately 20%, indicating no electrode/tissue contact.

28. The system of claim 26 wherein the pressure sensor is located on the electrode.

29. The system of claim 26 wherein the pressure sensor is located adjacent the electrode.

30. A method of assessing the adequacy of contact between an electrode and biological tissue within a biological organ having biological fluid therein, said method comprising:
  positioning the electrode in the biological fluid;
  obtaining a reference pressure value indicative of the pressure exerted on a region on or near the electrode;
  moving the electrode to a position proximal the biological tissue;
  obtaining an assessment pressure value by measuring the pressure exerted on the region on or near the electrode;
  analyzing the assessment pressure and the reference pressure; and
  indicating the state of electrode/tissue contact.

31. The method of claim 30 wherein analyzing the assessment pressure and the reference pressure comprises calculating the percentage difference between the two and indicating the state of electrode/tissue contact comprises:
  when the percentage difference is at least approximately 75%, indicating substantially complete electrode/tissue contact;
  when the percentage difference is in the approximate range between 20% and 75%, indicating partial electrode/tissue contact; and
  when the percentage difference is less than approximately 20%, indicating no electrode/tissue contact.

32. The method of claim 30 wherein the reference pressure value is the average of a plurality of reference pressure values obtained during a given time period.

33. The method of claim 30 wherein the assessment pressure value is the average value of a plurality of assessment pressure values obtained during a given time period.

34. A system for assessing the adequacy of contact between an electrode and biological tissue within a biological organ having biological fluid therein, said system comprising:
  an pressure sensor configured to provide assessment pressure values indicative of the pressure at the electrode; and
  a processor adapted to:
    sample a sequence of pressure values for a given time period; and
    monitor the sequence of pressure values for variations indicative of electrode/tissue contact.

35. The system of claim 34 wherein the processor is adapted to:
  determine an average pressure value based on a plurality of the pressure values;
  calculate the standard deviation of the pressure values relative the average pressure;
  calculate a deviation percentage;
  compare the deviation percentage to a plurality of predetermined contact assessment criteria; and
  provide an indication result, the criteria and results comprising, for a deviation percentage at least approximately 75%, indicating substantially complete electrode/tissue contact, for a deviation percentage in the approximate range between 25% and 75%, indicating partial electrode/tissue contact; and for a standard deviation percentage less than approximately 20%, indicating no electrode/tissue contact.

36. The system of claim 34 wherein the pressure sensor is located on the electrode.

37. The system of claim 34 wherein the pressure sensor is located adjacent the electrode.

38. A method of assessing the adequacy of contact between an electrode and biological tissue within a moving biological organ having biological fluid therein, said method comprising:
  positioning the electrode proximal the biological tissue;
  obtaining a sequence of pressure values by periodically measuring the pressure at the electrode during the time period; and
  monitoring the sequence of pressure values for variations indicative of electrode/tissue contact.

39. The method of claim 38 wherein monitoring the sequence of pressure values for variations indicative of electrode/tissue contact comprises:
  obtaining an average pressure value based on a plurality of the pressure values;
  calculating the standard deviation of the pressure values relative the average pressure;
  calculating a deviation percentage;
  when the deviation percentage is at least approximately 75%, indicating substantially complete electrode/tissue contact;
  when the deviation percentage is in the approximate range between 20% and 75%, indicating partial electrode/tissue contact; and
  when the deviation percentage is less than approximately 20%, indicating no electrode/tissue contact.

40. A method of assessing the adequacy of contact between a plurality of electrodes and biological tissue within a biological organ having biological fluid therein, said method comprising:
  obtaining a reference pressure value for each electrode by:
    positioning the plurality of electrodes in the biological fluid; and
    measuring the pressure exerted at each electrode by the biological fluid;
  moving the plurality electrodes to a position proximal the biological tissue; and
  for each electrode:
    obtaining an assessment pressure value by measuring the pressure exerted at each electrode;
    analyzing the assessment pressure and the reference pressure; and
    indicating the state of electrode/tissue contact.

41. A system for applying energy to biological tissue within a biological organ having fluid flowing therethrough, said system comprising:
  a generator for providing energy;
  a catheter carrying an electrode system at its distal segment, the distal segment having a tissue-contacting area adapted to be positioned in the biological organ and intended to contact the biological tissue, the electrode system adapted to receive energy from the generator;
  at least one pressure sensor associated with the distal segment, located within the tissue-contacting area and adapted to provide pressure data indicative of the pressure exerted on the distal segment at or near the pressure sensor; and a processor responsive to the pressure data and configured to analyze the pressure data and provide an indication of contact between the distal segment at or near the pressure sensor and the tissue; wherein the processor is adapted to:
convert the pressure data to a measured pressure value;
determine the percentage difference between a reference pressure value and the measured pressure value, the reference pressure value indicative of the pressure on the distal segment at or near the pressure sensor when the distal segment is positioned in the biological fluid; and
compare the percentage difference to a plurality of predetermined contact assessment criteria and provide an indication result, the criteria and results comprising, for a percentage difference of at least approximately 75%, indicating substantially complete contact, for a percentage difference in the approximate range between 25% and 75%, indicating partial contact, and for a percentage difference less than approximately 20%, indicating no contact.

42. A system for applying energy to biological tissue within a biological organ having fluid flowing therethrough, said system comprising:
a generator for providing energy;
a catheter carrying an electrode system at its distal segment, the distal segment having a tissue-contacting area adapted to be positioned in the biological organ and intended to contact the biological tissue, the electrode system adapted to receive energy from the generator;
at least one pressure sensor associated with the distal segment, located within the tissue-contacting area and adapted to provide pressure data indicative of the pressure exerted on the distal segment at or near the pressure sensor; and
a processor responsive to the pressure data and configured to analyze the pressure data and provide an indication of contact between the distal segment at or near the pressure sensor and the tissue;
wherein the pressure data comprises a sequence of pressure values indicative of the pressure on the distal segment over a period of time and the processor is adapted to monitor the sequence of pressure values for variations indicative of contact between the distal segment at or near the pressure sensor and the tissue.

43. A system for applying energy to biological tissue within a biological organ having fluid flowing therethrough, said system comprising:
a generator for providing energy;
a catheter carrying an electrode system at its distal segment, the distal segment having a tissue-contacting area adapted to be positioned in the biological organ and intended to contact the biological tissue and a fluid-contacting area intended to contact the fluid, the electrode system adapted to receive energy from the generator;
at least one pressure sensor associated with the distal segment, located within the tissue-contacting area and adapted to provide pressure data indicative of the pressure exerted on the distal segment at or near the pressure sensor;
at least one flow sensor positioned within the fluid-contacting area and adapted to provide flow-rate data indicative of the flow rate of the fluid through the biological organ; and
a processor responsive to the pressure data and configured to:
analyze the pressure data and provide an indication of contact between the distal segment at or near the pressure sensor and the tissue; and
receive the flow rate information, process the flow rate information to assess whether the fluid-flow rate is high or low and control the generator such that the generator provides energy of a first level to the electrode system during periods of high fluid-flow and energy of a second level, less than the first level, during periods of low fluid-flow.

44. A system for applying energy to biological tissue within a biological organ having fluid flowing therethrough, said system comprising:
a generator for providing energy;
a catheter carrying an electrode system at its distal segment, the distal segment having a tissue-contacting area adapted to be positioned in the biological organ and intended to contact the biological tissue and a fluid-contacting area intended to contact the fluid, the electrode system adapted to receive energy from the generator;
at least one pressure sensor associated with the distal segment, located within the tissue-contacting area and adapted to provide pressure data indicative of the pressure exerted on the distal segment at or near the pressure sensor;
at least one flow sensor positioned within the fluid-contacting area and adapted to provide flow-rate data indicative of the flow rate of the fluid through the biological organ; and
a processor responsive to the pressure data and configured to:
analyze the pressure data and provide an indication of contact between the distal segment at or near the pressure sensor and the tissue; and
control the generator such that the generator provides energy to the electrode system based on the flow-rate data.

45. A system for assessing the adequacy of contact between an electrode and biological tissue within a biological organ having biological fluid therein, said system comprising:
a pressure sensor located on the electrode and configured to provide a reference pressure indicative of the pressure at the electrode when the electrode is positioned in the biological fluid and configured to provide an assessment pressure indicative of the pressure at the electrode when the electrode is positioned proximal the biological tissue; and
a processor responsive to the reference and assessment pressure signals and configured to analyze the pressure signals and indicate the state of electrode/tissue contact.

46. A system for assessing the adequacy of contact between an electrode and biological tissue within a biological organ having biological fluid therein, said system comprising:
a pressure sensor located adjacent the electrode and configured to provide a reference pressure indicative of the pressure at the electrode when the electrode is positioned in the biological fluid and configured to provide an assessment pressure indicative of the pressure at the electrode when the electrode is positioned proximal the biological tissue; and
a processor responsive to the reference and assessment pressure signals and configured to analyze the pressure signals and indicate the state of electrode/tissue contact.

* * * * *

UNITED STATES PATENT AND TRADEMARK OFFICE
CERTIFICATE OF CORRECTION

PATENT NO. : 6,955,675 B2
APPLICATION NO. : 10/037663
DATED : October 18, 2005
INVENTOR(S) : Mudit K. Jain Page 1 of 1

It is certified that error appears in the above-identified patent and that said Letters Patent is hereby corrected as shown below:

Title Page, OTHER PUBLICATIONS, Item (56)
delete "Deparment" and insert --Department--;
delete "Ablaton" and insert --Ablation--.

Column 5,
Line 45, after "a power control system" insert --,-- (a comma).

Column 6,
Line 3, delete "senors" and insert --sensors--.

Column 17,
Line 28, delete "maybe" and insert --may be--.

Signed and Sealed this

Fifteenth Day of August, 2006

JON W. DUDAS
*Director of the United States Patent and Trademark Office*